United States Patent [19]

Saulnier et al.

[11] Patent Number: 4,935,504

[45] Date of Patent: Jun. 19, 1990

[54] EPIPODOPHYLLOTOXIN GLUCOSIDE 4'-ACYL DERIVATIVES

[75] Inventors: Mark G. Saulnier, Middletown; Dolatrai M. Vyas, Madison; David R. Langley, Meriden, all of Conn.

[73] Assignee: Bristol-Myers Company, New York, N.Y.

[21] Appl. No.: 277,901

[22] Filed: Dec. 2, 1988

Related U.S. Application Data

[63] Continuation-in-part of Ser. No. 135,129, Dec. 18, 1987, abandoned.

[51] Int. Cl.$^5$ ........................ C07H 15/26; A61K 31/70
[52] U.S. Cl. .................................... 536/18.1; 536/4.1; 536/18.2; 536/18.4; 536/17.2; 536/17.4; 536/17.5; 514/908
[58] Field of Search ..................... 536/18.1, 18.2, 17.2, 536/17.5, 17.4, 18.4, 4.1; 514/33, 35, 27, 908

[56] References Cited

U.S. PATENT DOCUMENTS

| | | | |
|---|---|---|---|
| 3,408,441 | 10/1968 | von Wartburg et al. | 536/18.1 |
| 3,524,844 | 8/1970 | Keller-Juslin et al. | 536/18.1 |
| 4,564,675 | 1/1986 | Kurabayashi et al. | 536/18.1 |
| 4,609,644 | 9/1986 | Nemec | 514/27 |
| 4,757,138 | 7/1988 | Fujii et al. | 536/18.1 |

FOREIGN PATENT DOCUMENTS

| | | |
|---|---|---|
| 956939 | 10/1974 | Canada . |
| 0111058 | 6/1984 | European Pat. Off. . |
| 162701 | 5/1985 | European Pat. Off. . |
| 226202 | 12/1986 | European Pat. Off. . |
| 219196 | 5/1983 | Japan . |
| 225096 | 6/1983 | Japan . |
| 150293 | 6/1988 | Japan . |
| 1205966 | 9/1970 | United Kingdom . |

OTHER PUBLICATIONS

McOmie (ED.); *Protective Groups in Organic Chemistry;* pp. 109–118 (1973).
J. Pharm. Sci., 1983, 72:1158–61.
Anti-Cancer Drug Design, 1987, 2:13–23.

*Primary Examiner*—Ronald W. Griffin
*Assistant Examiner*—Nancy S. Carson
*Attorney, Agent, or Firm*—Mollie M. Yang

[57] ABSTRACT

Novel 4'-esters, 4'-carbonates and 4'-carbamates of 4'-demethylepipodophyllotoxin glucosides are disclosed. These agents exhibit antitumor activity in animals.

43 Claims, No Drawings

EPIPODOPHYLLOTOXIN GLUCOSIDE 4'-ACYL DERIVATIVES

This application is a continuation-in-part of U.S. patent application, Ser. No. 135,129, filed Dec. 18, 1987, now abandoned.

BACKGROUND OF THE INVENTION

1. Field of the Invention

The present invention relates to 4'-acyl derivatives of 4'-demethylepipodophyllotoxin glucosides, to their use as antitumor agents, and to pharmaceutical compositions containing them. In particular, this invention relates to the 4'-ester, 4'-carbonates, and 4'-carbamates of 4'-demethylepipodophyllotoxin glucosides.

2. Description of Background Art

Etoposide (Ia) and teniposide (Ib) are clinically useful anti-tumor agents derived from the naturally occurring lignan, podophyllotoxin. The general class of compounds which includes etoposide and teniposide is sometimes referreed to as 4'-demethylepipodophyllotoxin glucosides; the 4'-position is indicated on formula (I) below.

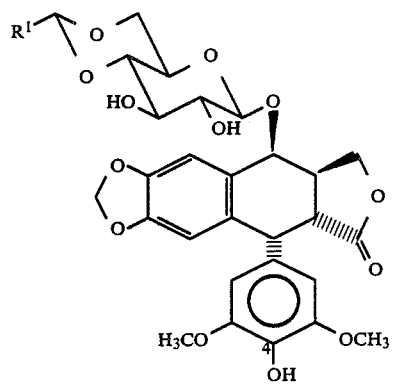

Ia: R = CH₃
Ib: R = 2-thienyl

4'-Demethylepipodophyllotoxin glucoside derivatives and the method for their preparation are disclosed in U.S. Pat. No. 3,408,441 to Wartburg et al and U.S. Pat. No. 3,524,844 to Keller-Juslen et al. These compounds, in particular etoposide and teniposide, serve as the starting materials for our preparation of the 4'-acyl derivatives of epipodophyllotoxin glucosides of the present invention.

A few 4'-esters and 4'-benzylcarbonates of 4'-demethylepipodophyllotoxin glucosides have been described in the literature as intermediates for the preparation of the corresponding 4'-demethylepipodophyllotoxin glucosides. However, the hydroxyl groups on the sugar moiety of these compounds are also protected and no biological activities have been reported therefor. Only one 4'-acyl derivative having free sugar hydroxyl groups has been reported.

Canadian Patent No. 956,939 discloses compounds of formula (II)

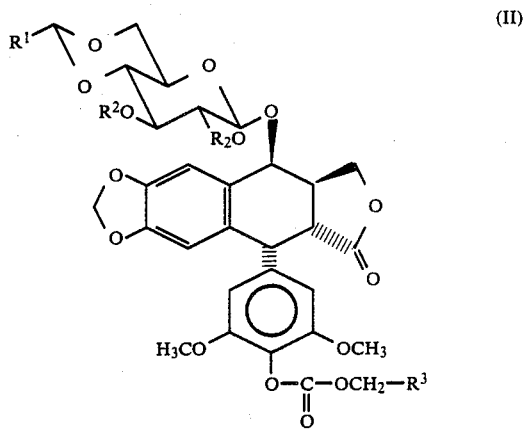

wherein $R^1$ is $C_{1-5}$ alkyl; $R^2$ is acetyl or formyl; and $R^3$ is phenyl or substituted phenyl; possible substituted phenyls mentioned but not exemplified are p-nitrophenyl and p-methoxyphenyl. There is also disclosed the process of selectively removing the $R^2$ groups of compounds of formula (III), wherein $R^1$ and $R^2$ are as above-defined, to give the corresponding 4'-benzyloxycarbonyl-4'-demethylepipodophyllotoxin glucosides (IV). Specifically exemplified is the preparation of 4'-benzyloxycarbonyl-4'-demethylepipodophyllotoxin-β-D-ethylidene glucoside (IV, $R^1$=CH₃).

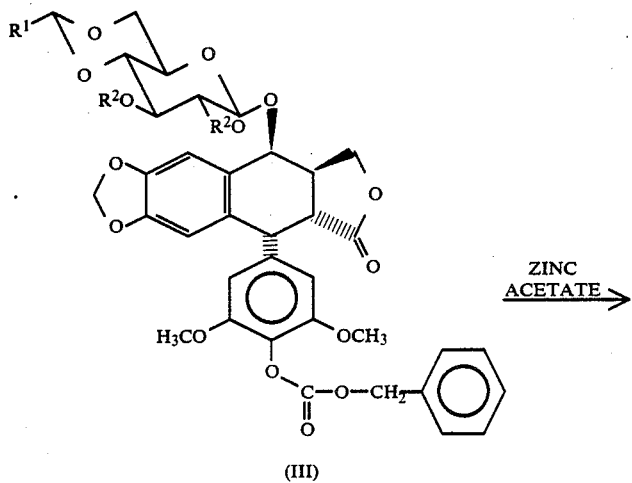

(III)

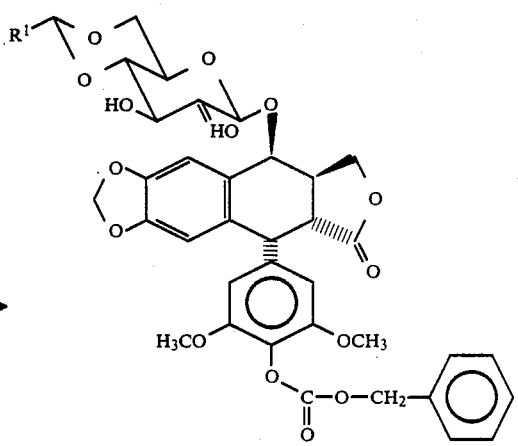

(IV)

U.S. Pat. No. 4,564,675 discloses compounds of the formula (V)

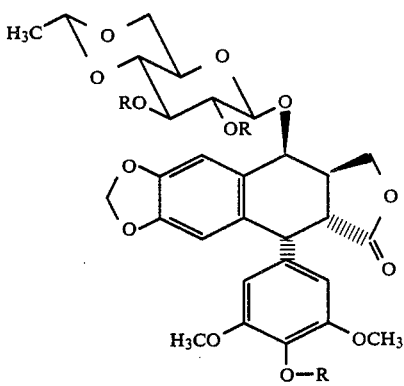

wherein R is —C(O)CH$_2$X, X is a halogen atom.

European Patent Application 162,701 discloses compounds of formula (VI)

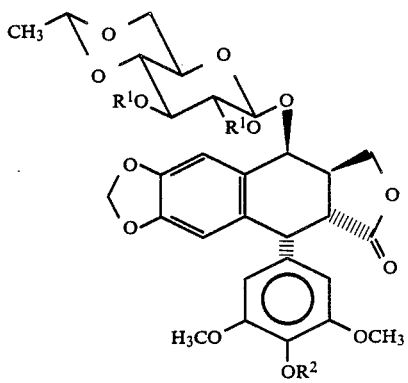

wherein R$^1$ and R$^2$ may be the same or different and each represent —C(O)CHX$_2$ or —C(O)CX$_3$ wherein X is a halogen atom.

Japanese Kokai 58/225,096 (Derwent Abst. No. 84-034268/06) and 58/219,196 (Derwent Abst. No. 84-027495/05) disclose compounds of formula (VII) and (VIII), respectively.

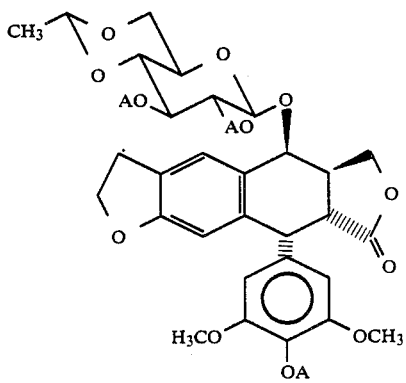

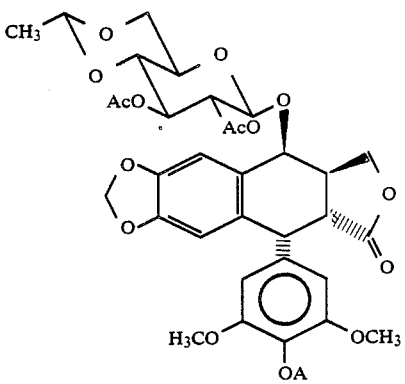

wherein A stands for —CO$_2$—CH$_2$—C(H)m(X)n wherein m is 0 to 2 and n is 1 to 3, m+n=3, and Ac is acetyl.

European Patent Application 226,202 discloses an intermediate for etoposide synthesis having the formula (IX)

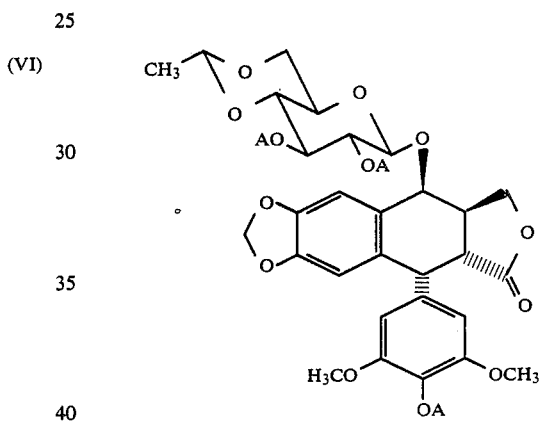

wherein A represents an acetyl group.

Esters of podophyllotoxin at the C-4 position (X) have been prepared and evaluated in P388 leukemeia. Although some esters showed antileukemic activity, they are nonetheless less active than the parent podophyllotoxin (J. Pharm. Sci., 1983, 72: 1158–61).

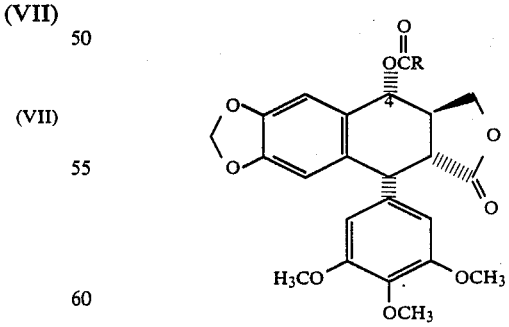

R is for example, methyl, ethylene, phenyl, phenethyl, phenoxy, and ethoxycarbonylbutyl.

C-4 esters of 4′-demethylepipodophyllotoxin (XI) have also been prepared and studied in vitro. They were found to behave like podophyllotoxin as microtubule assembly inhibitors, and did not show etoposide/teniposide-like activity (Anti-Cancer Drug Design, 1987. 2: 13-23).

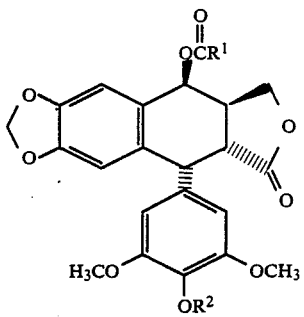

(XI)

$R^2$ is H and $R^1$ is for example methyl, phenyl, furyl; or $R^2$ is benzyloxycarbonyl and $R^1$ is 2-thienyl or 2,2-dimethylethylene.

It has now been discovered that surprisingly 4'-acyl-4'-demethylepipodophyllotoxin glucosides are potent antitumor agents in their own right and several 4'-acyl derivatives exhibit better activity than etoposide in the P388 leukemia model.

SUMMARY OF THE INVENTION

The present invention provides compounds having formula (XII)

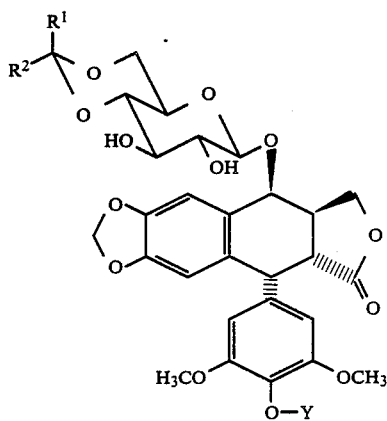

(XII)

wherein $R^1$ and $R^2$ are each $C_{1-10}$alkyl; or $R^1$, $R^2$, and the carbon to which they are attached represent $C_{5-6}$cycloalkyl; or $R^1$ is H and $R^2$ is selected from the group consisting of $C_{1-10}$alkyl, $C_{2-10}$alkenyl, $C_{3-6}$-cycloalkyl, furyl, thienyl, $C_{6-10}$aryl, and $C_{7-14}$aralkyl; and Y is —C(O)—$R^3$, —C(O)—X—$R^4$, or —C(O)—N$R^5R^6$, wherein X is oxygen or sulfur; $R^3$ is selected from the group consisting of H, $C_{1-10}$alkyl, $C_{2-20}$alkenyl, $C_{3-6}$cycloalkyl, $C_{6-10}$aryl, $C_{7-14}$aralkyl, and heteroaryl; each of the above groups is optionally substituted with one or more groups selected from hydroxy, $C_{1-6}$alkoxy, $C_{1-6}$alkanoyloxy, cyano, amino, $C_{1-6}$alkylamino, di($C_{1-6}$)alkylamino, quaternary ammonium, carboxy, $C_{1-6}$alkylthio, di($C_{1-6}$)alkylamino($C_{2-6}$)alkylthio, mercapto, mercaptothio, $C_{1-6}$alkanoylamino, nitro, $C_{1-6}$alkanoyl, carbamoyl, azido, halogen, $C_{1-6}$alkylsulfoxide, and sulfone; the substituents for the aryl, aralkyl, and heteroaryl groups may additionally include $C_{1-6}$alkyl; $R^4$ is selected from the group defined for $R^3$ with the exception that $R^4$ is not benzyl when X is oxygen, and $R^4$ is not H; or $R^4$ is anthraquinonyl-2-methylene; $R^5$ and $R^6$ are each independently selected from the group defined for $R^3$, or $R^5$ is H and $R^6$ is selected from the group consisting of amine, $C_{1-6}$alkylamine, and di($C_{1-6}$)alkylamine; or $R^5$, $R^6$ together with the N to which they are attached form a 3- to 6-membered ring; or a pharmaceutically acceptable salt thereof.

A preferred embodiment provides compounds of formula (XII) wherein $R^1$ is H and $R^2$ is methyl or 2-thienyl.

A further aspect of this invention provides intermediates 4'-demethylepipodophyllotoxin glucoside 4'-chloroformates of formula (XIII) wherein $R^1$ and $R^2$ are as previously defined.

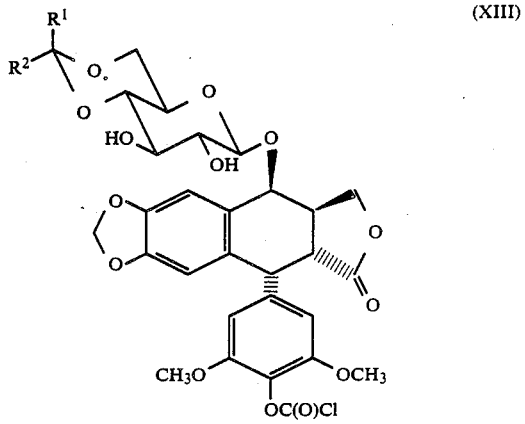

(XIII)

A further aspect of the present invention provides a method for inhibiting mammalian malignant tumors which comprises administering to an afflicted host a compound of formula (XII).

Yet a further aspect of the present invention provides a pharmaceutical composition comprising an antitumor effective amount of a compound of formula (XII) together with an inert pharmaceutical carrier or diluent.

DETAILED DESCRIPTION OF THE INVENTION

As used herein the term "alkyl" includes straight and branched carbon chains; "alkenyl" means straight or branched carbon chains having at least one double bond; "halo" or "halogen" includes fluoro, bromo, chloro, and iodo atoms; "heteroaryl" means an aromatic ring having at least one non-carbon atom in the ring including, but not limited to, pyridine, furan, thiophene, pyrrole, pyrimidine, quinoxaline and the like; and the notation "Z" refers to the cis-configuration of a double bond.

A preferred embodiment of the present invention provides compound of formula (XII) wherein $R^1$ is H, $R^2$ is selected from the group consisting of $C_{1-10}$ alkyl, phenyl and thienyl; and Y is —C(O)$R^3$, —C(O)X$R^4$, or —C(O)N$R^5R^6$ wherein X is oxygen or sulfur; $R^3$ is selected from the group consisting of $C_{3-6}$cycloalkyl, $C_{2-20}$alkenyl; $C_{1-10}$alkyl opt. substituted with one or more groups selected from the group consisting of halogen, azido, cyano, $C_{1-6}$alkylthio, di($C_{1-6}$)alkylamino, di($_{1-6}$)alkylamino($C_{2-6}$)alkylthio, quarternary ammonium, $C_{1-6}$alkylsulfoxide; phenyl opt. substituted with on or more groups selected from the group consisting of $C_{1-6}$alkyl, halogen, hydroxy, $C_{1-6}$alkoxy, mercapto, $C_{1-6}$alkylthio, cyano, and nitro; phenyl ($_{1-6}$)alkyl wherein the phenyl ring is opt. substituted with one or more groups selected from the above list of phenyl substituents; and pyridyl; $R^4$ is as defined above for $R^3$ with the exception that $R^4$ is not H and $R^4$ is not benzyl when X is oxygen; or $R^4$ is anthraquinonyl-2-methylene; and $R^5$ and $R^6$ are each independently selected from the group consisting of H, $C_{1-10}$alkyl opt. substituted with one or more groups selected from the group consisting of halogen, hydroxy, $C_{1-6}$alkoxy, mercapto, $C_{1-6}$alkylthio, cyano, amino, $C_{1-6}$alkylamino, di($C_{1-6}$)alkylamino, and azido; or $R^5$ is H and $R^6$ is selected from the group consisting of $C_{3-6}$-cycloalkyl, $C_{2-20}$alkenyl, phenyl opt. substituted with one or more groups selected from the list of phenyl substituents provided under $R^3$, phenyl ($C_{1-6}$)alkyl wherein the phenyl ring is opt. substituted with one or more groups selected from the list of phenyl substituent provided under $R^3$, amino, $C_{1-6}$alkylamino, di($C_{1-6}$)alkylamino, and pyridyl; or a pharmaceutically acceptable salt thereof.

A more preferred embodiment provides compounds of formula (XII) wherein Y is —C(O)—$R^3$ and $R^3$ is selected from the group consisting of $C_{1-10}$alkyl opt. substituted with one or more groups selected from halogen, azido, quaternary ammonium, $C_{1-6}$alkylthio, di($C_{1-6}$)alkylamino, di($C_{1-6}$)alkylamino($C_{2-6}$)alkylthiol and alkylsulfoxide; $C_{2-20}$alkenyl; phenyl; and pyridyl.

Another more preferred embodiment provides compounds of formula (XII) wherein Y is —C(O)—X$R^4$; and wherein X is oxygen or sulfur and $R^4$ is selected from the group consisting of $C_{1-10}$alkyl opt. substituted with di($C_{1-6}$)alkylamino or one or more halogen atoms; p-nitrobenzyl; and anthraqunionyl-2-methylene.

Yet another more preferred embodiment provides compounds of formula (XII) wherein Y is —C(O)—N$R^5R^6$ and $R^5$ and $R^6$ are independently selected from the group consisting of H, $C_{1-10}$alkyl opt. substituted with di($C_{1-6}$)alkylamino one or more halogen atom; or $R^5$ is H and $R^6$ is amino.

The phenol group of 4'-demethylepipodophyllotoxin glucosides may be acylated using methods generally known in the art. However, due to acid sensitivity of the glycosidic linkage and the tendency for base-promoted epimerization of the α-carbon of the lactone, strong acidic or basic reaction conditions are best avoided.

Thus esterification may be effected by employing the carboxylic acid $R^3CO_2H$ or an acylating equivalent derived therefrom, examples of which include symmetrical or mixed acid anhydride; active esters; active amide; and acid halide. When the carboxylic acid is used, the reaction is preferably conducted in the presence of a condensing agent such as dicyclohexylcarbodiimide. Acid halide is the preferred acylating agent and the reaction is conducted in a suitable anhydrous organic solvent such as acetonitrile, tetrahydrofuran, and acetone, and in the presence of a suitable base to neutralize the acid formed during the course of the reaction. Suitable bases are for example tertiary amine such as triethylamine, pyridine and diisopropylethylamine, and inorganic bases such as potassium carbonate and sodium carbonate.

4'-Carbonates may be obtained by reacting 4'-demethylepipodophyllotoxin glucosides with a haloformate ClC(O)X$R^4$ in the presence of a base. Alternatively, the 4'-phenol group of 4'-demethylepipodophyllotoxin glucoside is first converted into the 4'-phenol chloroformate intermediate (XIII) using phosgene or trichloromethyl chloroformate; the 4'-phenol chloroformate may then be coupled in situ with an alcohol or a thiol in the presence of a base to afford the desired products. Examples of suitable base are as recited above.

Analogously, 4'-carbamates are obtained when 4'-phenol chloroformate is condensed with an appropriate amine HN$R^5R^6$ either in the presence of a base, or an excess of the amine component may be employed to neutralize the acid generated.

In our experience, we have found acetonitrile to be the preferred solvent and diisopropylethylamine the preferred base for carrying out the acylation reactions.

The transformations described above are summarized in Scheme I.

Scheme I
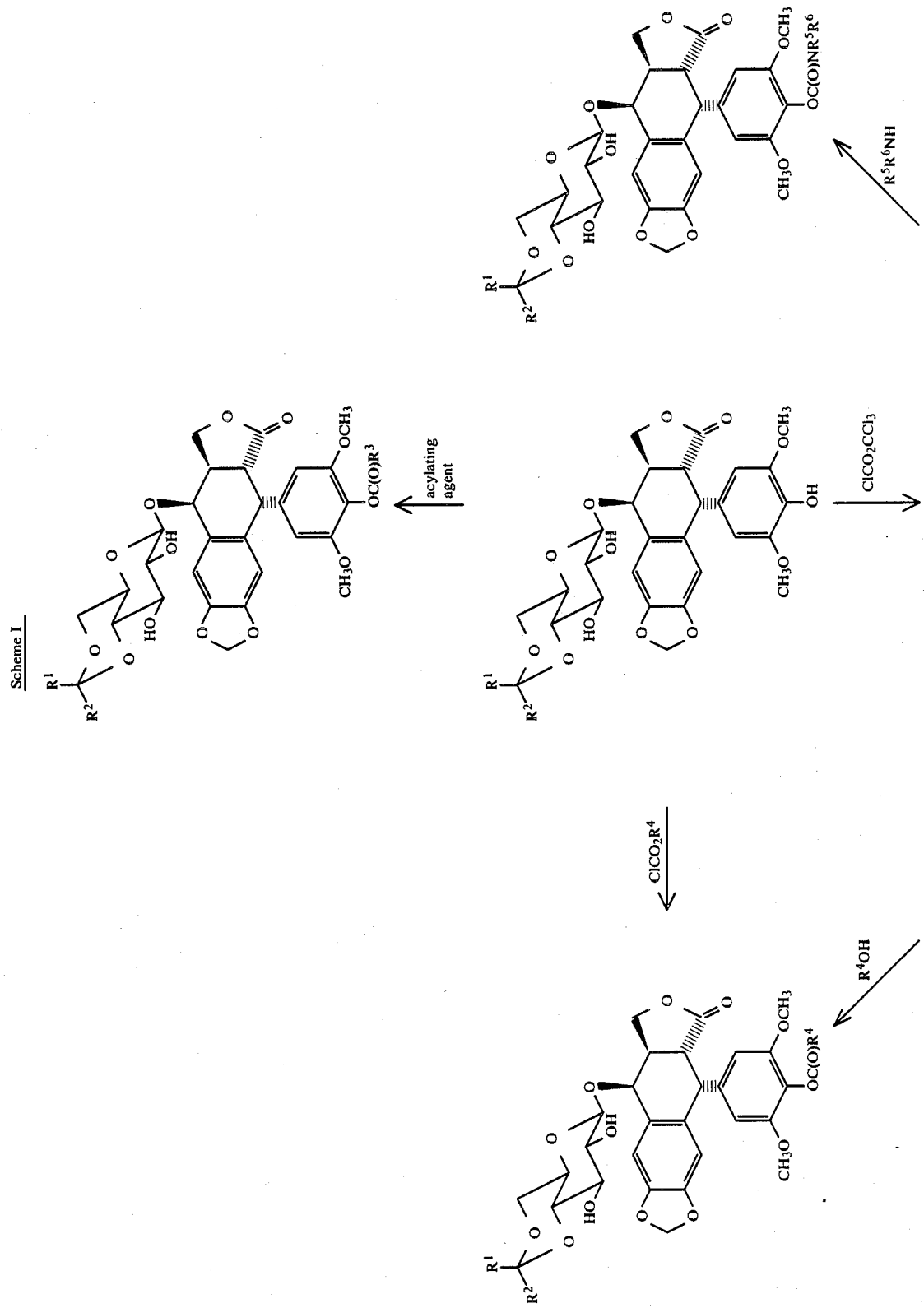

Scheme I -continued
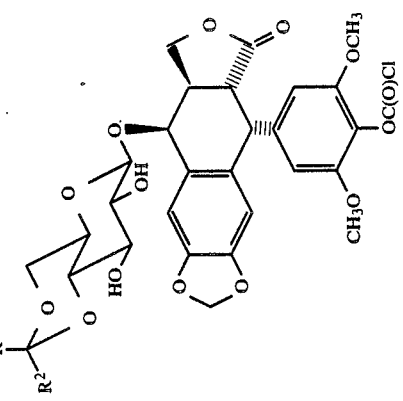

wherein the various R groups are as previously defined.

The course of the reaction may be monitored by thin layer chromatography by which the optimum reaction time may be judged by the appearance of product or the disappearance of starting material, or both. The reaction time may take from about 30 minutes to several days at temperatures from about −20° C. to about room temperature. The optimum reaction time and conditions will depend on the nature and reactivity of the particular reactants.

The final product may be recovered from the reaction mixture by standard techniques such as evaporating the reaction solvent, partitioning with water, precipitating, filtering, and drying of the product. The material may be further purified by conventional methods for example, recrystallization from appropriate solvents, or column chromatography or flash chromatography.

Some of the products obtained may be further modified to provide compounds within the scope of the present invention. For example, an haloalkyl ester may react with a nucleophile (Nu) to give the corresponding Nu-alkyl ester. Specific examples illustrating this aspect will be provided in the EXAMPLES section of this specification.

BIOLOGICAL ACTIVITY

Representative compounds of the present invention have been evaluated in transplantable murine P388 leukemia. Female $CDF_1$ mice were implanted intraperitoneally with a tumor inoculum of $10^6$ ascites cells of P388 leukemia and treated with various doses of a test compound. A group of four mice was used for each dose level. Ten mice treated with saline were included in each series of experiments as negative control and six etoposide treated mice were included as positive control. The drugs were administered intraperitoneally on days 5 and 8 (day 1 being the day of tumor implantation) or on days 1 and 5. The length of the experiments ranges from 30 days to 64 days. Several of the water soluble analogs were tested in an iv/iv system, i.e., the P388 leukemic cells were implanted intravenously and the test compounds administered intravenously; the positive control etoposide was given intraperitoneally. At the end of each experiment the number of survivors for each group was noted. The mean survival time for each group of mice was determined and antitumor activity was expressed as % T/C which is the ratio of the median survival time (MST) of drug-treated group to the MST of saline-treated control group. A compound showing a % T/C value of 125 or greater is generally considered to have significant antitumor activity in the P388 test. Table I presents the results of the above-described evaluation; included in the Table are the maximum % T/C and the dose showing the maximum effect, and other dose levels that showed survivors at the end of the test period.

TABLE 1

Antitumor activity against transplantable P388 leukemia in mice

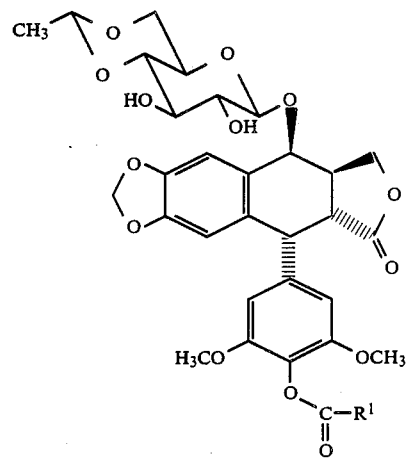

| $R^1$ | Dose[1] (mg/kg/dose) | Max. % T/C | Survivor (no./day) |
|---|---|---|---|
| —$CH_2(CH_2)_6CH\overset{Z}{=}CHCH_2CH\overset{Z}{=}CH(CH_2)_4CH_3$ | | | |
| in CMC[4] | 200 | 290 | |
| in DMSO | 200 | >395 | (2/d.46) |
|  | 50 | >345 | (2/d.46) |
| —$(CH_2)_2S(CH_2)_2N(CH_3)_2 \cdot HCl$ | | | |
| in saline | 200 | 215 | |
| Etoposide | 60 | 250 | |
| —$CH_2(CH_2)_2N(CH_3)_2 \cdot HCl$ | | | |
| in saline | 180 | >355 | (2/d.47)[3] |
| —$CH_2(CH_2)_2N(CH_3)_2$ | 90 | 245 | |
|  | 180 | 210 | (1/d.47) |
| 4-pyridyl.HCl (in saline) | 160 | 180 | |
| 4-pyridyl | 45 | 165 | |
| Etoposide | 80 | 260 | |
| —$CH_2(CH_2)_2Br$ | 45 | 205 | |
| —$CH_2(CH_2)_2I$ | 160 | 230 | |

TABLE 1-continued
Antitumor activity against transplantable P388 leukemia in mice

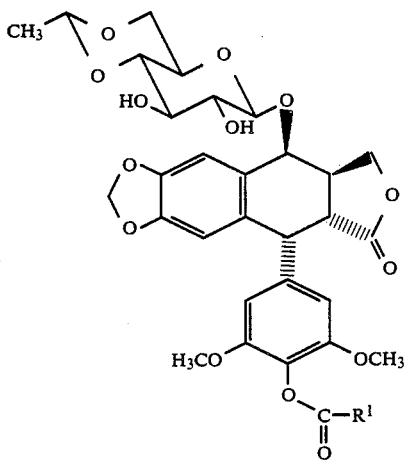

| R[1] | Dose[1] (mg/kg/dose) | Max. % T/C | Survivor (no./day) |
|---|---|---|---|
| —CH$_2$(CH$_2$)$_2$N$_3$ | 160 | 335 | |
| p-nitrobenzyloxy | 180 | 335 | |
| anthraquinone-2-methyloxy | 80 | 165 | |
| Etoposide | 80 | 295 | |
| —CH$_2$—Br | 40 | 205 | |
| Etoposide | 80 | >370 | (3/d.38) |
| —CH=CH$_2$ | 50 | 225 | |
| —CH$_2$(CH$_2$)$_5$CH$_3$ | 100 | 235 | |
| —OCH$_3$ | 70 | 235 | |
| Etoposide | 40 | 365 | |
| —OCH$_2$CCl$_3$ | 80[2] | 290 | (1/d.57) |
| Etoposide | 60[2] | >570 | (4/d.57) |
| phenyl | 60[2] | 330 | (1/d.45) |
| benzyloxy | 120[2] | 355 | (2/d.45) |
| Etoposide | 60[2] | 260 | (2/d.45) |
| —N(CH$_2$CH$_2$Cl)$_2$ | | | |
| in CMC | 200 | 145 | |
| in DMSO + H$_2$O | 100 | 210 | |
| Etoposide | | | |
| in CMC | 100 | 270 | |
| in DMSO + H$_2$O | 60 | 260 | |
| —NHNH$_2$ | 280 | 225 | |
| —O(CH$_2$)$_2$N(CH$_3$)$_2$ | 280 | 215 | |
| —NH(CH$_2$)$_2$N(CH$_3$)$_2$ | 140 | 190 | |
| —S(CH$_2$)$_2$N(CH$_3$)$_2$ | 280 | 230 | |
| Etoposide | 100 | 295 | (1/d.49) |
| —N(CH$_3$)$_2$ | 300 | 170 | |
| —NH$_2$ | 300 | 285 | (1/d.64) |
| Etoposide | 120 | 7510 | (3/d.64) |
| —NHCH$_3$ | 300 | 165 | |
| Etoposide | 150 | >480 | (5/d.48) |
| P388 Leukemic cells implanted intravenously. | | | |
| —O(CH$_2$)$_2$N(CH$_3$)$_2$.HCl (in H$_2$O) | 70[5] | 263 | |
| —NH(CH$_2$)$_2$N(CH$_3$)$_2$.HCl (in H$_2$O) | 35[5] | 175 | |
| —S(CH$_2$)$_2$N(CH$_3$)$_2$.HCl (in H$_2$O) | 70[5] | 256 | |
| Etoposide | 100 | 338 | |

[1] Drug administered intraperitoneally on days 5 and 8 unless otherwise specified.
[2] Drug administered intraperitoneally on days 1 and 5.
[3] Surviving mice free of tumor.
[4] All compounds are delivered as a suspension in H$_2$O + carboxymethylcellulose (CMC), with or without Tween 80, unless otherwise specified.
[5] Drug administered intravenously on days 5 and 8.

As indicated by the mouse tumor data provided above, compounds of present invention are useful as antitumor agents for inhibition of mammalian malignant tumors such as P-388 leukemia.

The invention includes within its scope pharmaceutical compositions containing an effective tumor-inhibiting amount of a compound of the present invention in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, optimal dosages and regiments for a given mammalian host can be readily ascertained by those skilled in the art. It will, of course, be appreciated that the actual dose used will vary according to the particular compound selected, composition formulated, the route of administration and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

In the following examples, proton nuclear magnetic resonance (NMR) spectra (using $CDCl_3$ or $D_2O$ as an internal reference) were recorded on a Bruker WM360 spectrometer. Infrared spectra (IR) were determined on a Perkin-Elmer 1800 Fourier Transform Infrared Spectrophotometer. "Flash chromatography" refers to the method described by Still (Still, W. C.; Kahan, M.; Mitra, A.; *J. Org. Chem.*, 1978, 43, 2923) and was carried out using E. Merck silica gel (230–400 mesh). The following examples serve only to illustrate the invention without limiting the scope of the invention which is defined by the claims.

EXAMPLE 1

Etoposide 4'-bromoacetate

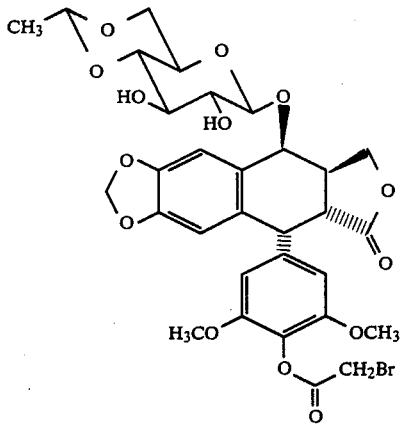

A magnetically stirred suspension of etoposide (2.05 g, 3.48 mmol) in dry acetonitrile (210 mL) was warmed briefly to give a nearly complete solution and then cooled to room temperature. To this mixture was added N,N-diisopropylethylamine (0.91 mL, 5.2 mmol) and then bromoacetyl chloride (0.63 g, 3.92 mmol) was added over 1 min via syringe. The mixture was stirred at room temperature for 30 min and then treated with additional bromoacetyl chloride (0.246 g, 1.56 mmol). The mixture was stirred for an additional 30 minutes then partitioned with 0.05M pH 7 phosphate buffer (250 mL) and ethyl acetate (300 mL). The organic layer was washed with brine (2×200 mL) and dried over $Na_2SO_4/MgSO_4$. Rotary evaporation of the solvent resulted in a dark solid which was purified by flash chromatography using a gradient elution of methylene chloride to 3–4% methanol in methylene chloride to provide 1.89 g (76.5%) of the pure title compound as a light yellow solid. Preparative TLC of a small sample using 5% methanol in methylene chloride provided the analytical sample as a colorless solid, mp 192°–196° C.

IR (KBr) 1775, 1605, 1515, 1490, 1340, 1238, 1130, 1040, 1010, 935, 700 cm$^{-1}$.

360 MHz $^1$H NMR (CDCl$_3$) δ 6.81 (s, 1H), 6.54 (s, 1H), 6.26 (s, 2H), 5.98 (d, 2H), 4.89 (d, 1H, J=3.4 Hz), 4.73 (q, 1H, J=5.0 Hz), 4.65–4.61 (m, 2H), 4.41 (dd, 1H), 4.32 (s, 1H), 4.22 (dd, 1H), 4.15 (dd, 1H), 4.07 (s, 1H), 3.73 (m, 1H), 3.66 (s, 6H), 3.56 (m, 1H), 3.43 (m, 1H), 3.34–3.31 (m, 2H), 3.27 (dd, 1H, J=5.2 and 14.1 Hz), 2.90–2.78 (m, 1H), 2.68 (d, 1H, J=2.1 Hz, OH), 2.40 (d, 1H, J=2.6 Hz, OH), 1.38 (d, 3H, J=5.0 Hz).

Anal. Calcd. for $C_{31}H_{33}BrO_{14}$: C, 52.48; H, 4.69. Found: C, 52.72; H, 4.77.

EXAMPLE 2

Etoposide 4'-(4-bromobutyrate)

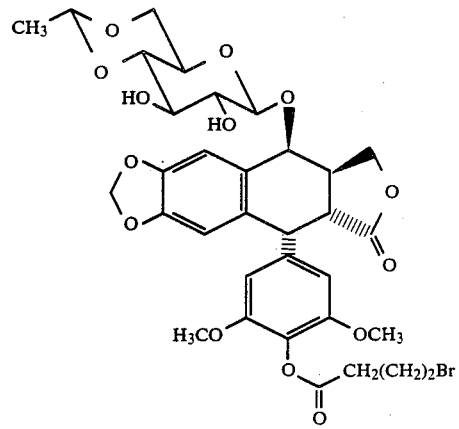

A nearly complete solution of etoposide (3.20 g, 5.44 mmol, prepared as described in Example 1) in dry acetonitrile (300 mL) was treated at room temperature with N,N-diisopropylethylamine (1.14 mL, 6.54 mmol) followed by the addition of 4-bromobutyryl chloride (1.16 g, 6.00 mmol) over 1 min. The mixture was stirred at room temperature for 1 h, cooled to −10° C., and then partitioned with 0.05M pH 7 phosphate buffer (400 mL) and ethyl acetate (500 mL). The organic layer was washed with water (150 mL) and brine (350 mL) and dried over $Na_2SO_4/MgSO_4$. Rotary evaporation afforded 4.1 g (100%) of the pure title compound as a colorless solid. Recrystallization from ethanol/hexane produced the analytical sample as a pure white solid.

IR (KBr) 1769, 1602, 1506, 1486, 1465, 1421, 1386, 1362, 1338, 1237, 1159, 1131, 1099, 1078, 1039, 1004, 933 cm$^{-1}$.

360 MHz $^1$H NMR (CDCl$_3$) δ 6.81 (s, 1H), 6.54 (s, 1H), 6.26 (brs, 2H), 5.98 (d, 2H), 4.89 (d, 1H, J=3.3 Hz), 4.74 (q, 1H, J=5.1 Hz), 4.66–4.62 (m, 2H), 4.41 (dd, 1H), 4.24–4.13 (m, 2H), 3.72 (m, 1H), 3.65 (s, 6H), 3.58 (m, 1H), 3.55 (t, 2H), 3.43 (m, 1H), 3.34–3.23 (m, 3H), 2.90–2.80 (m, 1H), 2.75 (t, 2H), 2.63 (d, 1H, J=2.1 Hz, OH), 2.33 (d, 1H, J=2.4 Hz, OH), 2.27 (t, 2H), 1.38 (d, 3H, J=5.1 Hz).

Anal. Calcd for $C_{33}H_{37}BrO_{14}$: C, 53.74; H, 5.06; Br, 1083. Found: C, 54.03; H, 5.13; Br, 10.80.

EXAMPLE 3

Etoposide 4'-(4-iodobutyrate)

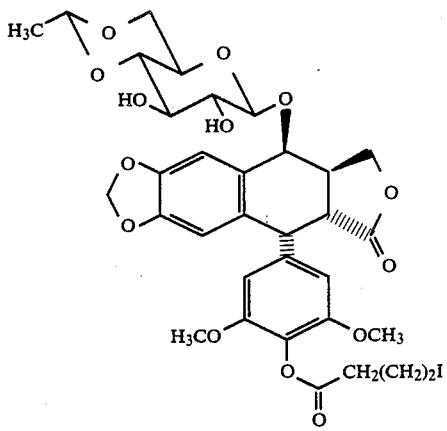

A magnetically stirred solution of etoposide 4'-(4-bromobutyrate) (3.55 g, 4.81 mmol) in reagent acetone (175 mL) was treated with sodium iodide (12.8 g, 85.4 mmol) and the mixture was heated under nitrogen atmosphere at 48° C. for 22 h and then refluxed for 1 h. The mixture was cooled to room temperature, filtered through a pad of celite washed 3 times with acetone) and the filtrate was evaporated in-vacuo. The residue was partitioned in methylene chloride (300 mL) and water (250 mL) and the aqueous portion was further extracted with methylene chloride (2×50 mL). The combined organic extracts were washed with water (150 mL) and brine (150 mL) and dried over $Na_2SO_4/MgSO_4$. Rotary evaporation followed by further drying at 0.1 torr provided the pure title compound as a light yellow solid in quantitative yield.

360 MHz $^1$H NMR (CDCl$_3$) δ 6.81 (s, 1H), 6.54 (s, 1H), 6.26 (brs, 2H), 5.98 (d, 2H), 4.89 (d, 1H, J=3.2 Hz), 4.74 (q, 1H, J=5.0 Hz), 4.65-4.61 (m, 2H), 4.41 (dd, 1H), 4.22 (dd, 1H), 4.15 (dd, 1H, J=3.5 and 10.6 Hz), 3.74 (m, 1H), 3.66 (s, 6H), 3.56 (m, 1H), 3.42 (m, 1H), 3.35-3.24 (m, 3H), 3.31 (t, 2H), 2.90-2.79 (m, 1H), 2.69 (t, 2H), 2.23 (t, 2H), 1.38 (d, 3H, J=5.0 Hz).

EXAMPLE 4

Etoposide 4'-(4-azidobutyrate)

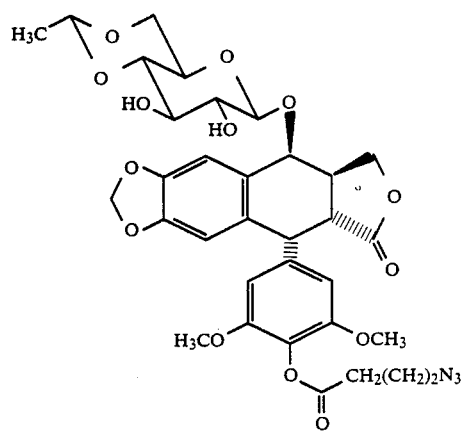

A solution of etoposide 4'-(4-iodobutyrate) (115 mg, 0.147 mmol) in dry dimethylformamide (2 mL) was treated with dry lithium azide (16.5 mg, 0.337 mmol) and stirred under nitrogen atmosphere for 28 h at room temperature. The mixture was diluted with ethyl acetate (65 mL) and partitioned with 0.05M pH 7 phosphate buffer (50 mL). The organic layer was washed with water (4×25 mL) and brine (2×40 mL) and dried over $Na_2SO_4/MgSO_4$. Rotary evaporation followed by further drying at 0.1 torr provided 100 mg (98%) of the pure title compound as a colorless solid.

IR (KBr) 2102, 1768, 1736, 1602, 1486, 1337, 1237, 1158, 1133, 1096, 1078, 1038, 932, 699 cm$^{-1}$.

360 MHz $^1$H NMR (CDCl$_3$) δ 6.81 (s, 1H), 6.54 (s, 1H), 6.26 (brs, 2H), 5.98 (d, 2H), 4.89 (d, 1H, J=3.3 Hz), 4.73 (q, 1H, J=5.1 Hz), 4.65-4.62 (m, 2H), 4.41 (dd, 1H, J=9.2 and 10.5 Hz), 4.24-4.13 (m, 2H), 3.74 (m, 1H), 3.65 (s, 6H), 3.56 (m, 1H), 3.43 (m, 1H), 3.42 (t, 2H), 3.34-3.30 (m, 2H), 3.26 (dd, 1H, J=5.2 and 14.1 Hz), 2.90-2.80 (m, 1H), 2.67 (t, 2H), 1.99 (t, 2H), 1.38 (d, 3H, J=5.1 Hz).

EXAMPLE 5

Etoposide 4'-(4-aminobutyrate) Acetic Acid Salt

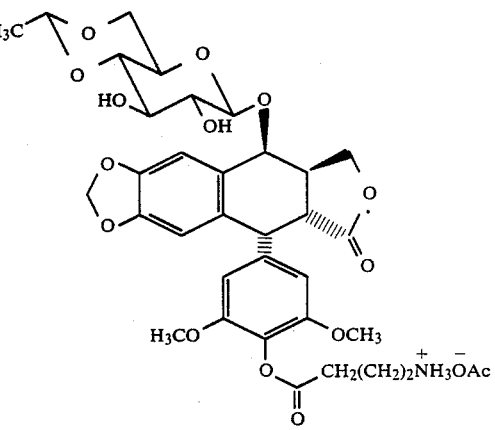

A solution of etoposide 4'-(4-azidobutyrate) (300 mg, 0.429 mmol) in ethyl acetate (30 mL) was treated with 460 mg of Lindlar catalyst (5% Pd on calcium carbonate poisoned with lead) and glacial acetic acid (10 mL). The mixture was then hydrogenated at 35 psi for 2.5 h. The mixture was filtered through a pad of celite and the filtrate was slowly added to a 2:1 mixture of ether and n-pentane (100 mL). The resulting white precipitate was collected by filtration, washed with ether and dried at 0.1 torr to yield 38.1 mg (12.1%) of the pure title compound.

Partial 360 MHz $^1$H NMR (CDCl$_3$) δ 6.80 (s, 1H), 6.53 (s, 1H), 6.24 (brs, 2H), 5.98 (d, 2H), 4.89 (d, 1H), 4.73 (q, 1H), 4.65 (d, 1H), 4.59 (d, 1H), 4.40 (m, 1H), 4.22–4.11 (m, 2H), 3.74 (s, 6H), 3.73 (m, 1H), 3.65 (s, 2H), 3.56 (m, 1H), 3.47–3.21 (m, 6H, 2.92–2.82 (m,H), 2.31 (t, 2H), 2.08 (s, 3H), 1.38 (d, 3H).

EXAMPLE 6

Etoposide 4'-methylthioacetate

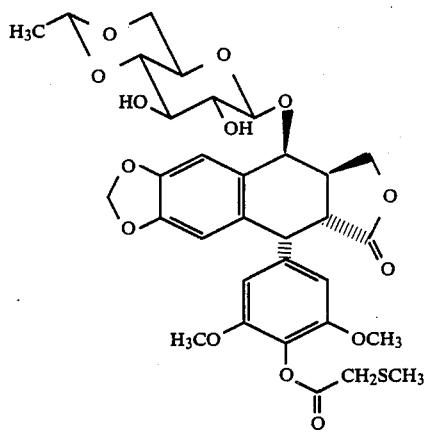

Etoposide (3.10 g, 5.27 mmol), dicyclohexylcarbodiimide (DCC 1.76 g, 8.53 mmol) and methylthioacetic acid (792 mg, 7.46 mmol) was treated under nitrogen atmosphere with dry tetrahydrofuran (125 mL) and the resulting colorless solution was stirred at room temperature for 100 h and additional methylthioacetic acid (180 mg) was added. After stirring at room temperature for 17 h, additional DCC (250 mg) was added and the reaction mixture was kept at room temperature for 48 h and then concentrated in-vacuo. The resulting white solid was treated with ethyl acetate (175 mL), stirred for 5 min, and filtered through a pad of celite. The solids were washed with ethyl acetate (4×75 mL) and the combined filtrate was partitioned with 0.25M pH 7 phosphate buffer (300 mL) and then washed with water (250 mL) and brine (2×200 mL) and dried over Na$_2$SO$_4$/MgSO$_4$. Rotary evaporation followed by flash chromatography on silica gel using a methylene chloride/methanol gradient from 100:0 to 98:2 produced 1.85 g (52%) of the pure title compound as a white solid.

360 MHz $^1$H NMR (CDCl$_3$) δ 6.81 (s, 1H), 6.54 (s, 1H), 6.27 (brs, 2H), 5.97 (d, 2H), 4.89 (d, 1H, J=3.4 Hz), 4.74 (q, 1H, J=5 Hz), 4.65–4.62 (m, 2H), 4.41 (dd, 1H), 4.22 (dd, 1H), 4.17 (dd, 1H), 3.72 (m, 1H), 3.66 (s, 6H), 3.56 (m, 1H), 3.44 (m, 1H), 3.43 (s, 2H), 3.34–3.31 (m, 1H), 3.26 (dd, 1H, J=14.1 and 5.2 Hz), 2.90–2.80 (m, 1H), 2.64 (d, 1H, J-2.2 Hz, OH), 2.38 (d, 1H, J=2.5 Hz, OH), 2.27 (s, 3H), 1.38 (d, 3H, J=5 Hz).

EXAMPLE 7

Etoposide 4'-([4-dimethylamino]butyrate)

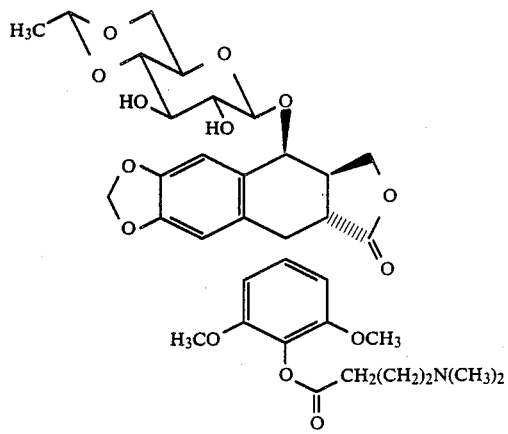

A solution of etoposide (2.60 g, 4.41 mmol) in dry acetonitrile (220 mL) was treated at room temperature with N,N-diisopropylethylamine (2.20 mL, 12.06 mmol) and then this solution was added quickly to 4-dimethylaminobutyryl chloride hydrochloride (prepared from 0.82 g (4.89 mmol) of the corresponding acid hydrochloride and thionyl chloride). The mixture was stirred at room temperature for 1.5 h and poured into cold saturated aqueous sodium bicarbonate (400 mL), ethyl acetate (400 mL), and brine (60 mL). The organic layer was washed with water (3×50 mL) and brine (2×150 mL) and dried over Na$_2$SO$_4$. Rotary evaporation followed by flash chromatography on silica gel using 5–10% methanol in methylene chloride provided 1.28 g (41%) of the pure title compound as a tan solid.

IR (KBr) 1770, 1602, 1507, 1486, 1466, 1421, 1337, 1236, 1160, 1130, 1078, 1038, 1003, 932 cm$^{-1}$.

360 MHz $^1$H NMR (CDCl$_3$) δ 6.81 (s, 1H), 6.53 (s, 1H), 6.26 (brs, 2H), 5.97 (d, 2H), 4.89 (d, 1H, J=3.4 Hz), 4.74 (q, 1H, J=5 Hz), 4.65–4.61 (m, 2H), 4.41 (dd, 1H), 4.22 (dd, 1H), 4.15 (dd, 1H), J=3.9 and 10.4 Hz), 3.74 (m, 1H), 3.65 (s, 6H), 3.56 (m, 1H), 3.42 (m, 1H), 3.35–3.31 (m, 2H), 3.27 (dd, 1H, J=5.2 and 14.1 Hz), 2.90–2.80 (m, 1H), 2.63 (t, 2H), 2.40–2.36 (m, 2H), 2.40 (s, 6H), 2.01 (m, 2H), 1.38 (d, 3H, J=5 Hz).

mass spectrum (FAB), m/e, 702 (M$^+$+H). C$_{35}$H$_{43}$NO$_{14}$ requires M$^+$, 701.

EXAMPLE 8

Etoposide 4'-([4-dimethylamino]butyrate) hydrochloride

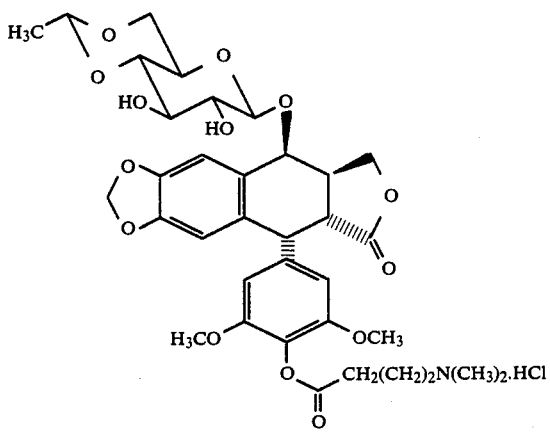

A magnetically stirred solution of etoposide 4'-(4-dimethylamino butyrate) (155 mg, 0.221 mmol) in dry methylene chloride (7 mL) was cooled to 0° C. and treated slowly over 2 min with a solution of hydrogen chloride (1.0M in Et$_2$O, 250 μlit, 0.250 mmol). After 10 min at 0° C., the solution was concentrated under N$_2$ to about 2 mL. This solution was then slowly added to 60 mL of rapidly stirred dry Et$_2$O. The resulting white precipitate was collected by filtration, washed with ether and dried at 0.1 torr to afford 146 mg (89%) of the pure title compound as an off-white solid. This material is soluble in both water and organic solvents.

360 MHz $^1$H NMR (CDCl$_3$) 12.65 (brs, 1H), 6.82 (s, 1H), 6.53 (s, 1H), 6.27 (brs, 2H), 5.98 (d, 1H), 4.89 (d, 1H, J=3.6 Hz), 4.73 (q, 1H, J=4.9 Hz), 4.65–4.62 (m, 2H), 4.42 (dd, 1H), 4.22 (dd, 1H), 4.15 (dd, 1H, J=3.9 and 10.4 Hz), 3.74 (m, 1H), 3.66 (s, 6H), 3.56 (m, 1H), 3.42 (m, 1H), 3.34–3.24 (m, 3H), 3.10 (m, 2H), 2.90–2.80 (m, 1H), 2.76 (s, 6H), 2.72 (t, 2H), 2.25 (m, 2H), 1.38 (d, 3H, J=4.9 Hz).

EXAMPLE 9

Etoposide 4'-(isonicotinoate)

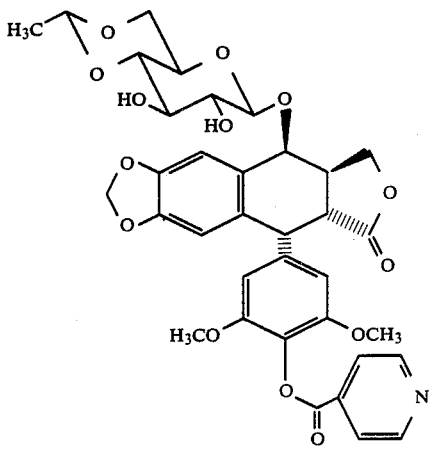

To a magnetically stirred solution of etoposide (2.15 g, 3.65 mmol) in dry acetonitrile (210 mL) was added N,N-diisopropylethylamine (1.65 mL, 9.47 mmol) followed by isonicotinoyl chloride hydrochloride (0.75 g, 4.21 mmol). After the addition of more N,N-diisopropylethylamine (0.70 mL), the mixture was stirred at room temperature for 9 days and the partitioned with pH 7 phosphate buffer (300 mL), ethyl acetate (400 mL) and brine (75 mL). The organic layer was washed with water (2×50 mL) and brine (2×100 mL), dried over Na$_2$SO$_4$, and then filtered through celite. The filtrate was concentrated to a volume of 225 mL and methylene chloride (20 mL) was added thereto. Hexane was then added to the solution until it appeared slightly cloudy. The mixture was stored at 0° C. for 1.5 h. The product was collected by filtration and dried in-vacuo to give 885 mg (35%) of the pure title compound as a white solid. Concentration of the mother liquor provided the additional material which was contaminated by only a small amount of etoposide.

360 MHz $^1$H NMR (CDCl$_3$) δ 8.83 (brs, 2H), 8.07 (brs, 2H), 6.82 (s, 1H), 6.57 (s, 1H), 6.32 (brs, 2H), 5.98 (ABq, 2H), 4.91 (d, 1H, J=3.5 Hz), 4.74 (q, 1H, J=4.9 Hz), 4.67–4.65 (m, 2H), 4.43 (dd, 1H), 4.24 (dd, 1H), 4.15 (dd, 1H), 3.73 (m, 1H), 3.65 (s, 6H), 3.54 (m, 1H), 3.44 (dd, 1H), 3.36–3.26 (m, 3H), 2.95–2.85 (m, 1H), 1.38 (d, 3H, J=4.9 Hz).

EXAMPLE 10

Etoposide 4'-(isonicotinoate) hydrochloride

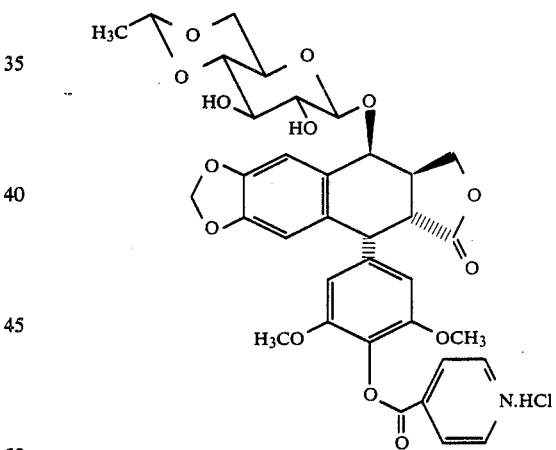

A magnetically stirred solution of etoposide 4'-(isonicotinoate) (compound of example 9, 215 mg, 0.310 mmol) in dry methylene chloride (3 mL) was cooled to 0° C. under nitrogen atmosphere and treated slowly over 5 min with a solution of hydrogen chloride (1.0M in ether; 300 μlit, 0.300 mmol). The solvent was decanted and the remaining yellow solid was washed with methylene chloride (2×2 mL) and dried in-vacuo to provide 175 mg (80%) of the pure title compound.

360 MHz $^1$H NMR (d6-DMSO) δ 8.88 (d, 2H, J=5.7 Hz), 7.96 (d, 2H, J=5.7 Hz), 7.03 (s, 1H), 6.58 (s, 1H), 6.35 (brs, 2H), 6.16 (brs, 2H), 4.95 (d, 1H, J=3.2 Hz), 4.72 (q, 1H, J=4.9 Hz), 4.64 (d, 1H, J=5.5 Hz), 4.59 (d, 1H, J=7.7 Hz), 4.07 (dd, 1H, J=10.1 and 4.7 Hz), 3.61 (s, 6H), 3.50 (dd, 1H), 3.39–2.89 (m, 6H), 1.23 (d, 3H, J=4.9 Hz).

EXAMPLE 11

Etoposide 4'-(linoleate)

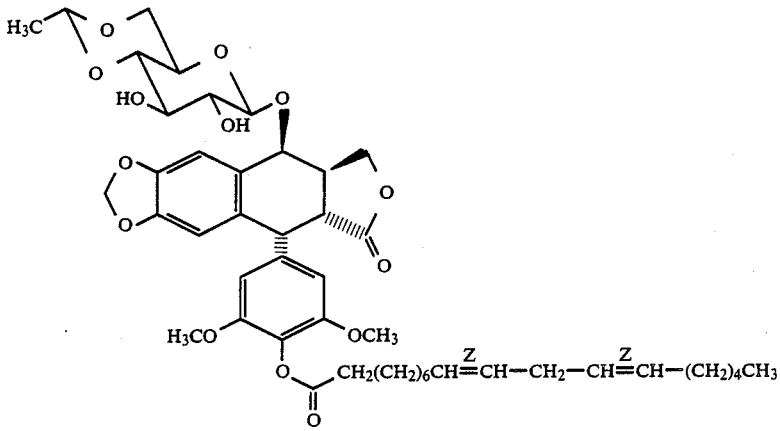

To a solution of etoposide (2.29 g, 3.89 mmol) and N,N-diisopropylethylamine (1.60 mL, 9.19 mmol) in dry acetonitrile (210 mL) at room temperature was added quickly a solution of linoleic acid chloride in 20 mL of dry acetonitrile (linoleic acid chloride was prepared from 1.17 g (4.17 mmol) of linoleic acid and 1.10 mL of oxalyl chloride in methylene chloride; following evaporation in-vacuo and drying at 0.1 torr, the crude acid chloride was dissolved in dry acetonitrile and used immediately). The mixture was stirred at room temperature for 45 min and partitioned with pH 7 phosphate buffer (250 mL) and ethyl acetate (300 mL). The organic layer was washed with water (100 mL) and brine (150 mL) and dried over Na$_2$SO$_4$/MgSO$_4$. Rotary evaporation gave a colorless solid which was dried further at 0.1 torr. A solution of the solid in methylene chloride (15 mL) was slowly added to 145 mL of hexane under stirring. The resulting white precipitate was collected by filtration, washed with hexane and dried at 0.1 torr to provide 3.25 g (98%) of the pure title compound as a colorless solid.

IR (KBr) 2929, 1770, 1601, 1506, 1486, 1466, 1421, 1337, 1236, 1159, 1132, 1098, 1078, 1038, 1003, 933 cm$^{-1}$.

360 MHz $^1$H NMR (CDCl$_3$) δ 6.81 (s, 1H), 6.54 (s, 1H), 6.25 (brs, 2H), 5.97 (d, 2H), 5.37-5.28 (m, 4H), 4.88 (d, 1H, J=3.4 Hz), 4.73 (q, 1H, J=5.0 Hz), 4.66-4.61 (m, 2H), 4.41 (dd, 1H), 4.21 (dd, 1H), 4.15 (dd, 1H, J=4.2 and 10.4 Hz), 3.74 (m, 1H), 3.64 (s, 6H), 3.56 (m, 1H), 3.42 (dd, 1H), 3.34-3.31 (m, 2H), 3.25 (dd, 1H, J=5.2 and 14.1 Hz), 2.92-2.82 (m, 1H), 2.76-2.72 (m, 2H), 2.67 (brs, 1H, OH), 2.55 (t, 2H, J=7.4 Hz), 2.39 (brs, 1H, OH), 2.07-1.97 (m, 4H), 1.75-1.27 (m, 14H), 1.37 (d, 3H, J=5.0 Hz), 0.86 (t, 3H, J=6.7 Hz).

Mass spectrum (FAB), m/e, 850 (M+), 645 (M+- sugar). C$_{47}$H$_{62}$O$_{14}$ requires M+, 850.

Anal. Calcd for C$_{47}$H$_{62}$O$_{14}$: C, 66.34; H, 7.34. Found: C, 65.67; H, 7.39.

EXAMPLE 12

Etoposide 4'-acrylate

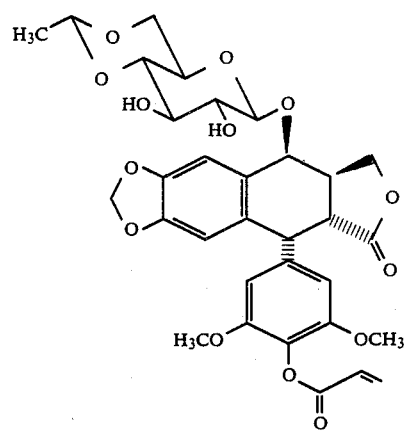

Using the procedure described in Example 1, etoposide (1.86 g, 3.16 mmol), N,N-diisopropylethylamine (0.81 mL, 4.65 mmol), and acryloyl chloride (0.35 mL, 4.3 mmol) in dry acetonitrile (200 mL) produced 1.73 g (85%) of the pure title compound following crystallization of the crude material from methylene chloride/petroleum ether.

360 MHz $^1$H NMR (CDCl$_3$) δ 6.80 (s, 1H), 6.55 (m, 2H), 6.34 (m, 1H), 6.27 (s, 2H), 5.96 (m, 3H), 4.88 (d, 1H), 4.73 (q, 1H), 4.61 (m, 2H), 4.43 (dd, 1H), 4.22 (dd, 1H), 4.15 (dd, 1H), 3.70 (m, 1H), 3.64 (s, 6H), 3.55 (m, 1H), 3.41 (m, 1H), 3.29 (m, 3H), 2.85 (m, 1H), 1.36 (d, 3H).

EXAMPLE 13

Etoposide 4'-[3-[(2-dimethylamino)ethylthio]propionate]hydrochloride

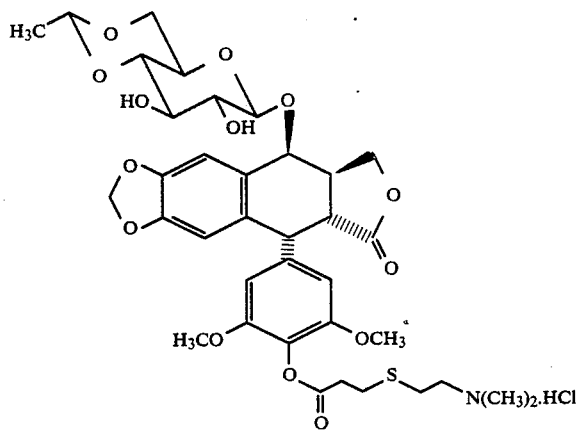

A solution of etoposide 4'-acrylate (compound of Example 12, 625 mg, 0.97 mmol) in ethanol (25 mL) was treated with 2-dimethylaminoethanethiol hydrochloride (305 mg, 2.14 mmol) and the mixture was stirred at room temperature for 64 h. The solvent was evaporated in-vacuo and the crude product so obtained was purified by flash chromatography on silica gel using 10% methanol in methylene chloride as eluant to provide 610 mg (84%) of the pure title compound following precipitation of the chromatographed material from petroleum ether.

IR (KBr) 1775, 1607, 1510, 1495, 1240, 1135 cm$^{-1}$.

360 MHz $^1$H NMR (CDCl$_3$) δ 6.81 (s, 1H), 6.52 (s, 1H), 6.24 (s, 2H), 5.96 (dd, 2H), 4.89 (d, 1H), 4.72 (q, 1H), 4.60 (m, 2H), 4.40 (dd, 1H), 4.21 (dd, 1H), 4.16 (dd, 1H), 3.68 (m, 1H), 3.64 (s, 6H), 3.55 (m, 1H), 3.39 (m, 1H), 3.29 (m, 3H), 2.87 (s, 6H), 2.66 (m, 2H), 2.51 (m, 2H), 1.36 (d, 3H).

Mass spectrum (FAB), m/e, 748 (M$^+$+H). C$_{36}$H$_{45}$NO$_{14}$S requires (M$^+$) 747.

EXAMPLE 14

Etoposide 4'-octanoate

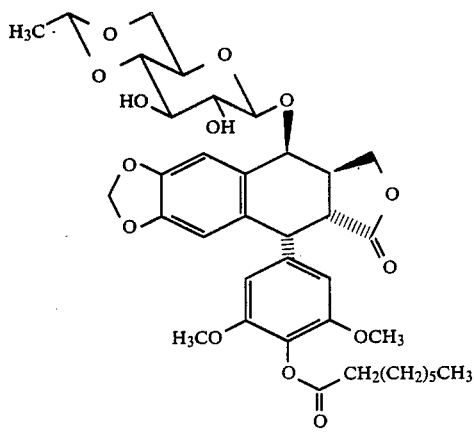

Using the procedure described in Example 1, etoposide (1.80 g, 3.06 mmol), N,N-diisopropylethylamine (0.63 mL, 3.62 mmol) and octanoyl chloride (0.63 mL, 3.69 mmol) in dry acetonitrile (250 mL) produced 2.03 g (93%) of the pure title compound following flash chromatography and precipitation from ether/petroleum ether.

360 MHz $^1$H NMR (CDCl$_3$) δ 6.80 (s, 1H), 6.53 (s, 1H), 6.24 (brs, 2H), 5.96 (d, 2H), 4.88 (d, 1H, J=3.5 Hz), 4.72 (q, 1H, J=5 Hz), 4.60 (m, 2H), 4.40 (dd, 1H), 4.21 (dd, 1H), 4.13 (dd, 1H), 3.69 (m, 1H), 3.58 (s, 6H), 3.57 (m, 1H), 3.40 (dd, 1H), 3.31 (m, 2H), 3.28 (dd, 1H), 2.86 (m, 1H), 2.56 (t, 2H), 1.73 (m, 2H), 1.37 (m, 5H), 1.29 (m, 6H), 0.85 (t, 3H).

EXAMPLE 15

Etoposide 4'-benzoate

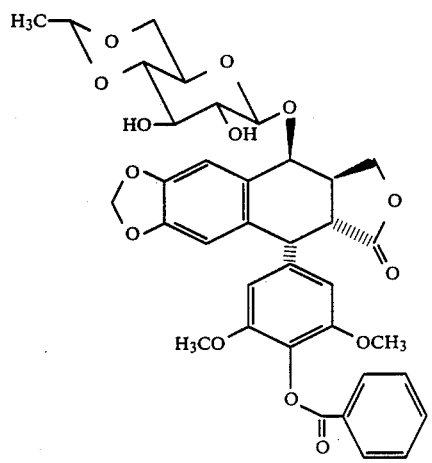

A magnetically stirred mixture of etoposide (133.5 mg, 0.227 mmol) and anhydrous potassium carbonate (379 mg, 2.74 mmol) in reagent acetone (12 mL) was cooled to 0° C. under nitrogen atmosphere and treated with benzoyl chloride (88 μlit, 0.758 mmol). The mixture was stirred at 0°-5° C. for 4.5 h, filtered and the filtrate was concentrated in-vacuo. Chromatography on silica gel using 5% methanol in methylene chloride provided 94.1 mg (60%) of the pure title compound as a colorless solid.

360 MHz $^1$H NMR (CDCl$_3$) δ 8.19 (d, 2H), 7.59 (t, 1H), 7.47 (m, 2H), 6.82 (s, 1H), 6.54 (s, 1H), 6.32 (brs, 2H), 5.97 (d, 2H), 4.88 (d, 1H), 4.72 (q, 1H), 4.63 (m, 2H), 4.43 (dd, 1H), 4.24 (dd, 1H), 4.17 (dd, 1H), 3.69 (m, 1H), 3.59 (s, 6H), 3.58 (m, 1H), 3.41 (dd, 1H), 3.31 (m, 2H), 3.28 (dd, 1H), 2.85 (m, 1H), 1.38 (d, 3H).

EXAMPLE 16

Etoposide 4′-benzyl carbonate

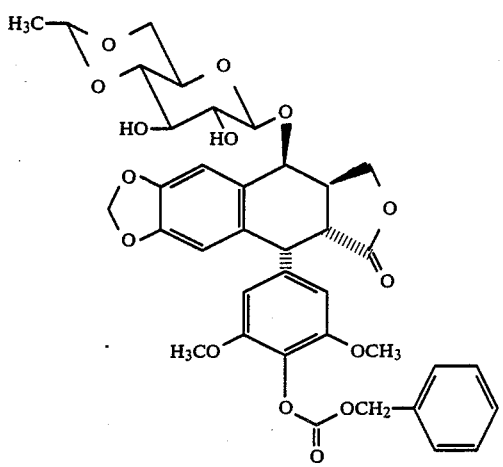

A magnetically stirred mixture of etoposide (343.5 mg, 0.584 mmol) and anhydrous potassium carbonate (903 mg, 6.53 mmol) in reagent acetone was cooled to 0° C. under nitrogen atmosphere and treated with benzyl chloroformate (261 μlit, 312 mg, 1.83 mmol). The mixture was stirred at room temperature for 25 h and then filtered. The filtrate was concentrated in-vacuo and chromatographed on silica gel using 4% methanol in methylene chloride to provide 244 mg (58%) of the pure title compound as a colorless solid.

360 MHz $^1$H NMR (CDCl$_3$) δ 7.43–7.32 (m, 5H), 6.81 (s, 1H), 6.53 (s, 1H), 6.26 (s, 2H), 5.97 (d, 2H), 5.24 (s, 2H), 4.88 (d, 1H), 4.73 (q, 1H), 4.65–4.59 (m, 2H), 4.41 (dd, 1H), 4.22 (dd, 1H), 4.15 (dd, 1H), 3.71 (m, 1H), 3.64 (s, 6H), 3.56 (m, 1H), 3.41 (m, 1H), 3.31 (m, 2H), 3.27 (dd, 1H), 2.85 (m, 1H), 2.73 (d, 1H, OH), 2.55 (d, 1H, OH), 1.37 (d, 3H).

EXAMPLE 17

Etoposide 4′-(2,2,2-trichloroethyl) carbonate

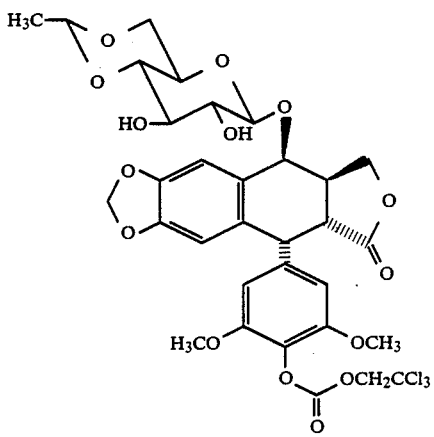

Using the procedure described in example 16 with etoposide (374 mg, 0.635 mmol), anhydrous potassium carbonate (1.00 g, 7.25 mmol), and reagent acetone (25 mL), but substituting 2,2,2-trichloroethyl chloroformate (98.5 μlit, 0.715 mmol) for the benzyl chloroformate, there was obtained 245 mg (50%) of the desired title compound as a colorless solid.

360 MHz $^1$H NMR (CDCl$_3$) δ 6.81 (s, 1H), 6.54 (s, 1H), 6.28 (s, 2H), 5.97 (d, 2H), 4.88 (d, 1H), 4.83 (s, 2H), 4.74 (q, 1H), 4.63 (m, 2H), 4.42 (dd, 1H), 4.24 (dd, 1H), 4.16 (dd, 1H), 3.71 (m, 1H), 3.67 (s, 6H), 3.56 (m, 1H), 3.41 (m, 1H), 3.32 (m, 2H), 3.27 (dd, 1H), 2.85 (m, 1H), 2.67 (d, 1H, OH), 2.43 (d, 1H, OH), 1.37 (d, 3H).

EXAMPLE 18

Etoposide 4′-methyl carbonate

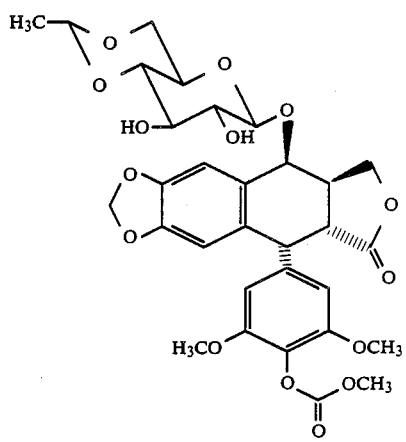

A magnetically stirred mixture of etoposide (340 mg, 0.578 mmol) in methylene chloride (10 mL) was treated with anhydrous pyridine (1.0 mL) and then methyl chloroformate (190 μlit, 2.46 mmol). The mixture was stirred at room temperature for 18 h and partitioned with water and methylene chloride. The organic extract was washed with brine and dried over MgSO$_4$. Flash chromatogrpahy on silica gel using 5% methanol in methylene chloride followed by precipitation from methylene chloride/petroleum ether produced 95 mg (28%) of the pure title compound as a colorless solid.

360 MHz $^1$H NMR (CDCl$_3$) δ6.81 (s, 1H), 6.54 (s, 1H), 6.26 (s, 2H), 5.97 (d, 2H), 4.88 (d, 1H, J=3.5 Hz), 4.74 (q, 1H), 4.63 (m, 2H), 4.41 (dd, 1H), 4.24 (dd, 1H), 4.14 (dd, 1H), 3.86 (s, 3H), 3.71 (m, 1H), 3.68 (s, 6H), 3.53 (m, 1H), 3.45 (m, 1H), 3.32 (m, 2H), 3.27 (dd, 1H), 2.85 (m, 1H), 2.65 (d, 1H, OH), 2.37 (d, 1H, OH), 1.37 (d, 3H).

mass spectrum (FAB), m/e, 647 (M$^+$+H). C$_{31}$H$_{34}$O$_{15}$ requires M$^+$, 646.

EXAMPLE 19

Etoposide 4'-[2-(methyl)anthraquinone]carbonate

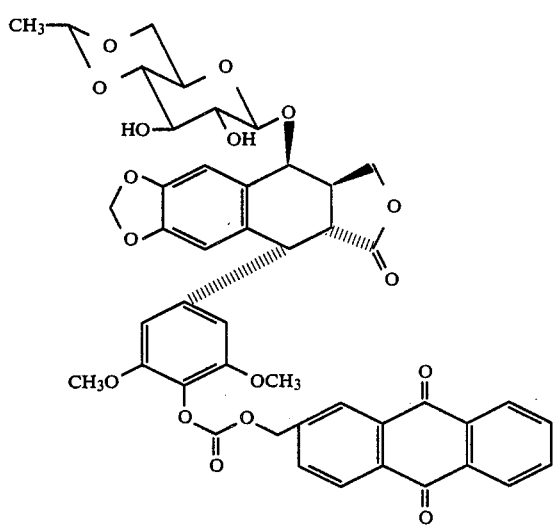

To a magnetically stirred solution of diphosgene (145 μlit, 1.12 mmol) in anhydrous tetrahydrofuran (3 mL) under nitrogen atmosphere at 0° C. was added slowly over 3 min a solution of 2-(hydroxymethyl) anthraquinone (505 mg, 2.12 mmol) in dry tetrahydrofuran (21 mL) containing anhydrous pyridine (180 μlit, 2.23 mmol). The mixture was stirred at 0° C. for 5 min and at room temperature for 15 min and then to this solution at 0° C. (containing a white precipitate) was rapidly added via cannula a cold solution of etoposide (1.17 g, 1.99 mmol) in dry tetrahydrofuran (25 mL) containing N,N-diisopropylethylamine (420 μlit, 2.41 mmol). The mixture was stirred for 65 h under nitrogen atmosphere in the dark, warmed to 40° C., stirred, for 6 h more and partitioned with pH 7 phosphate buffer (25 mL), water (150 mL), and ethyl acetate (350 mL). The organic layer was washed with water (100 mL) and brine (150 mL) and dried over $Na_2SO_4/MgSO_4$. Rotary evaporation followed by flash chromatography on silica gel using gradient elution from 0 to 2% MeOH in methylene chloride provided 97.2 mg (6%) of the pure title compound as a yellow solid.

IR (Kbr) 1774 (lactone), 1733 (carbonate), 1678 (quinone), 1602, 1506, 1486, 1464, 1454, 1435, 1422, 1386, 1327, 1294, 1237, 1160, 1131, 1096, 1078, 933 cm$^{-1}$.

360 MHz $^1$H NMR (CDCl$_3$) δ8.33–8.28 (m, 4H), 7.84–7.78 (m, 3H), 6.81 (s, 1H), 6.53 (s, 1H), 6.28 (s, 2H), 5.97 (dd, 2H), 5.40 (s, 2H), 4.89 (d, 1H, J=3.5 Hz), 4.73 (q, 1H, J=4.9 Hz), 4.66–4.62 (m, 2H), 4.41 (dd, 1H), 4.22 (dd, 1H), 4.15 (dd, 1H, J=10.4 and 4.2 Hz), 3.71 (m, 1H), 3.69 (s, 6H), 3.56 (m, 1H), 3.41 (m, 1H), 3.34–3.31 (m, 2H), 3.26 (dd, 1H), J=14.0 and 5.2 Hz), 2.89–2.83 (m, 1H), 2.61 (d, 1H, OH, J=2.2 Hz), 2.30 (d, 1H, OH, J=2.4 Hz), 1.38 (d, 3H, J=4.9 Hz).

mass spectrum (FAB), m/e, 853 (M$^+$+H), 808, 723, 646, 587. C$_{45}$H$_{40}$O$_{17}$ requires M$^+$, 852.

EXAMPLE 20

Etoposide 4'-(4-nitrobenzyl) carbonate

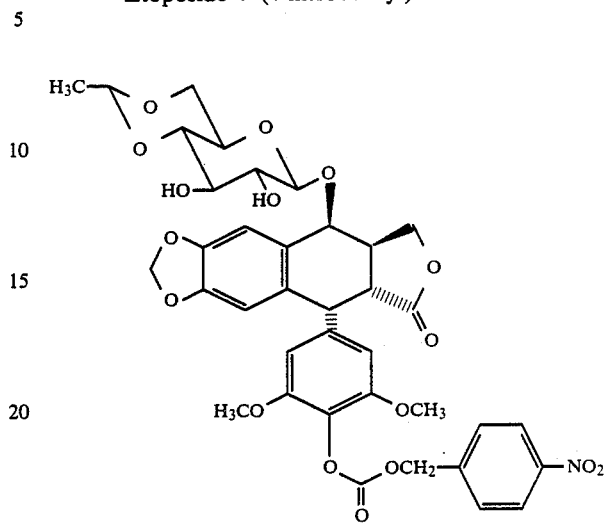

A magnetically stirred suspension of etoposide (5.19 g, 8.82 mmol) in dry acetonitrile (700 mL) was treated at room temperature under nitrogen atmosphere with N,N-diisopropylethylamine (2.15 mL, 12.3 mmol) followed by the addition of 4-nitrobenzyl chloroformate (2.20 g, 10.2 mmol). All of the material slowly dissolved over 30 min to give a pale yellow solution which was allowed to stir at room temperature for 16 h. The solvent was removed in-vacuo and the residue was dissolved in ethyl acetate (500 mL) and partitioned with pH 7 phosphate buffer (200 mL) and dried over Na$_2$SO$_4$/MgSO$_4$. Rotary evaporation gave a solid which was dissolved in ethyl acetate (50 mL), filtered through celite. The celite was washed with fresh ethyl acetate (2×25 ml) and the combined filtrate was slowly added to 600 mL of rapidly stirred hexanes. The resulting precipitate was collected by filtration, washed with hexanes and dried at 50° C./0.5 torr to give 6.73 g (99%) of the pure title compound as a very pale yellow solid.

360 MHz $^1$H NMR (CDCl$_3$) δ8.22 (d, 2H, J=8.6 Hz), 7.56 (d, 2H, J=8.6 Hz), 6.81 (s, 1H), 6.52 (s, 1H), 6.27 (s, 2H), 5.98 (d, 2H), 5.32 (s, 2H), 4.89 (d, 1H, J=3.4 Hz), 4.73 (q, 1H, J=5.0 Hz), 4.65–4.61 (m, 2H), 4.42 (dd, 1H), 4.22 (dd, 1H), 4.15 (dd, 1H, J=10.5 and 4.0 Hz), 3.74 (m, 1H), 3.66 (s, 6H), 3.56 (m, 1H), 3.43 (m, 1H), 3.36–3.31 (m, 2H), 3.27 (dd, 1H, J=14.1 and 5.2 Hz), 2.89–2.78 (m, 1H), 2.64 (brs, 1H, OH), 2.37 (brs, 1H, OH), 1.38 (d, 3H, J=5.0 Hz).

EXAMPLE 21

Etoposide 4'-[N,N-bis(2-chloroethyl)]carbamate

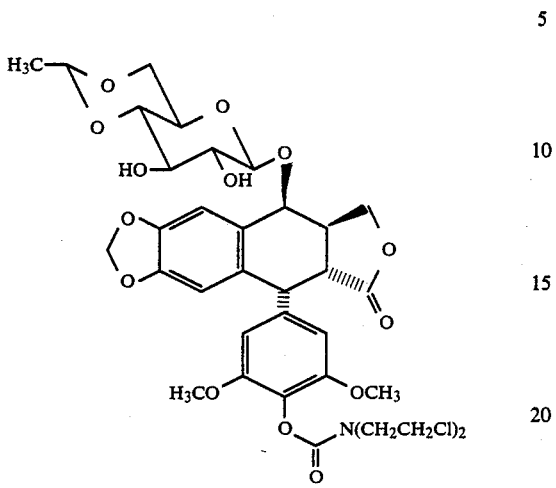

A magnetically stirred solution of etoposide (2.10 g, 3.57 mmol) in dry acetonitrile (215 mL) was treated under nitrogen atmosphere at room temperature with N,N-diisopropylethylamine (0.85 mL, 4.88 mmol) and cooled to 0° C. To this solution was added over 1 min, neat via syringe, diphosgene (361.5 mg, 215 μlit, 1.83 mmol). After 5 min at 0° C., the reaction mixture was quenched by the addition of solid bis(2-chloroethyl)amine hydrochloride (750 mg, 4.20 mmol) followed immediately by the addition of N,N-diisopropylethylamine (1.60 mL, 9.19 mmol). The reaction mixture was stirred at 0° C. for 1.5 h and then at room temperature for 1 h and partitioned with pH 5.0 phosphate buffer (300 mL), ethyl acetate (400 mL), and brine (100 mL). The organic phase was washed with brine (3×150 mL) and dried over $Na_2SO_4/MgSO_4$. Rotary evaporation followed by flash chromatography on silica gel using gradient elution with 0 to 4% methanol in methylene chloride provided 1.71 g (63%) of the pure title compound as a colorless solid.

IR (KBr) 1773, 1728, 1602, 1506, 1486, 1468, 1420, 1338, 1236, 1191, 1160, 1130, 1097, 1077, 1038, 1003, 933, 890, 864 $cm^{-1}$.

360 MHz $^1H$ NMR ($CDCl_3$) δ6.80 (s, 1H), 6.52 (s, 1H), 6.26 (brs, 2H), 5.97 (d, 2H), 4.89 (d, 1H, J=3.3 Hz), 4.73 (q, 1H, J=4.8 Hz), 4.64-4.61 (m, 2H), 4.41 (dd, 1H), 4.23-4.14 (m, 2H), 3.81-3.67 (m, 9H), 3.67 (s, 6H), 3.57 (m, 1H), 3.42 (m, 1H), 3.34-3.31 (m, 2H), 3.27 (dd, 1H, J=14.1 and 5.2 Hz), 2.90-2.80 (m, 1H), 2.75 (brs, 1H, OH), 2.55 (brs, 1H, OH), 1.38 (d, 3H, J=4.8 Hz).

mass spectrum (FAB), m/e, 756 ($M^+ +H$), 550 (M-sugar). $C_{34}H_{39}Cl_2NO_{14}$ requires $M^+$, 755.

high resolution mass spectrum (FAB), m/e, 755.1725 ($M^+$). $C_{34}H_{39}Cl_2NO_{14}$ requires $M^+$, 755.1747.

EXAMPLE 22

Etoposide 4'-methylcarbamate

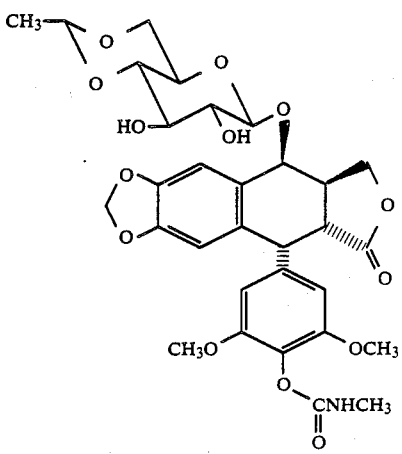

A magnetically stirred solution of etoposide (2.00 g, 3.40 mmol) in dry acetonitrile (200 ml) was treated with N,N-diisopropylethylamine (1.66 ml, 9.53 mmol) and cooled under $N_2$ to 0° C. To this solution was added phosgene (1.93M in toluene; 2.20 ml, 4.42 mmol) rapidly via syringe. The reaction mixture was stirred for 10 min. at 0° C. and then added rapidly to 40% aqueous methylamine (5.86 ml, 6.80 mmol). The mixture was stirred for 30 min. at 0° C. and then partitioned with ethyl acetate (350 ml) and 0.1N hydrochloric acid (150 ml). The organic layer was washed with water (200 ml) and brine (200 ml) and dried over magnesium sulfate. Rotary evaporation followed by flash chromatography on silica gel using 2% methanol in methylene chloride gave 673 mg (31%) of the pure title compound.

IR (KBr) 1775 (sh), 1740, 1604, 1517, 1490, 1425, 1335, 1238, 1168, 1134, 1104, 1080, 1040, 1010, 936 $cm^{-1}$.

300 MHz $^1H$ NMr ($CDCl_3$) δ6.79 (s, 1H, 6.53 (s, 1H), 6.24 (s, 2H), 5.96 (d, 2H), 5.01 (t, 1H), 4.87 (d, 1H), 4.72 (q, 1H), 4.64-4.60 (m, 2H), 4.40 (m, 1H), 4.23-4.12 (m, 2H), 3.76-3.70 (m, 1H), 3.66 (s, 6H), 3.54 (m, 1H), 3.42 (m, 1H), 3.37-4.20 (m, 3H), 2.90-2.82 (m, 1H9, 2.83 (d, 3H), 2.70 (br s, 1H, OH), 2.47 (br s, 1H, OH), 1.36 (d, 3H).

Mass spectrum (FAB), m/e, 646.2111 ($M^+ +H$), $C_{31}H_{35}NO_{14}$ requires 646.2136.

EXAMPLE 23

Etoposide 4'-carbamate

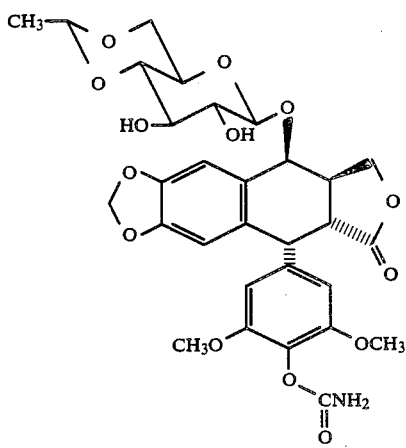

The 4'-chloroformate of etoposide was generated in situ from 2.00 g of etoposide according to the procedure given in Example 22, quenched with aqueous ammonium hydroxide (29.8% NH3, 237 μl, 3.74 mmol), and the resulting reacting mixture was worked-up and purified as described in Example 22 to afford 0.99 g (46%) of the pure title compound as a colorless solid.

IR (KBr) 1776, 1742 (sh), 1608, 1510, 1490, 1425, 1350, 1238 1165, 1133, 1100, 1080, 1038, 1010, 935 cm$^{-1}$.

300 MHz $^1$H NMR (CDCl$_3$) δ6.80 (s, 1H), 6.53 (s, 1H), 6.24 (s, 2H), 5.95 (d, 2H), 5.94 (br s, 2H), 4.88 (d, 1H), 4.73 (q, 1H), 4.63–4.59 (m, 2H), 4.39 (m, 1H), 4.20 (m, 1H), 4.17 (dd, 1H), 3.71 (m, 1H), 3.67 (s, 6H), 3.54 (m, 1H), 3.38 (m, 1H), 3.33–3.23 (m, 3H), 2.90–2.82 (m, 1H), 2.77 (br s, 1H, OH), 2.58 (br s, 1H, OH), 1.36 (d, 3H).

Mass spectrum (FAB), m/e 632.1973 (M$^+$+H). C$_{30}$H$_{33}$NO$_{14}$ requires 632.1979.

EXAMPLE 24

Etoposide 4'-dimethylcarbamate

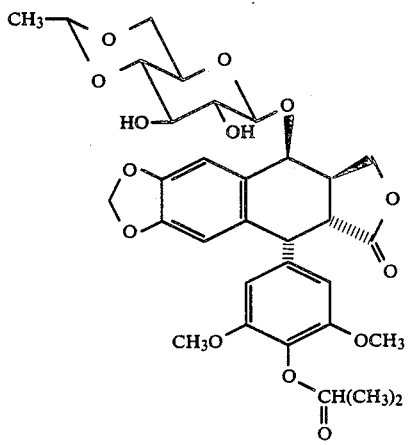

The 4'-chloroformate of etoposide was generated in situ from 2.00 g of etoposide according to the procedure given in Example 22, and quenched with neat dimethylamine (0.60 ml, 8.9 mmol). The resulting reaction mixture was worked-up as in Example 22 and the product flash chromatographed on silica gel using 3:1 ethyl acetate/hexane to afford 1.12 g (50%) of the pue title as a colorless solid.

IR (KBr) 1775, 1733, 1605, 1514, 1492, 1395, 1340, 1239, 1165, 1132, 1100, 1080, 1040, 1007, 935 cm$^{-1}$.

300 MHz $^1$H NMR (CDCl$_3$) δ6.79 (s, 1H), 6.54 (s, 1H), 6.24 (brs, 2H), 5.96 (d, 2H), 4.88 (d, 1H, J=3.4 Hz), 4.73 (q, 1H, J=5 Hz), 4.62 (dd, 1H), 4.43–4.06 (m, 2H), 3.68 (m, 1H), 3.66 (s, 6H), 3.56 (m, 1H), 3.39 (m, 1H), 3.33–3.23 (m, 3H), 3.08 (br s, 3H), 2.96 (br s, 3H), 2.91–2.82 (m, 1H), 2.76 (d, 1H, J=2.2 Hz, OH), 2.54 (d, 1H, J=2.6 Hz, OH), 1.37 (d, 3H, J=5 Hz).

Mass spectrum (FAB), m/e, 660 (M$^+$+H). C$_{32}$H$_{37}$NO$_{14}$ requires M$^+$=659.

EXAMPLE 25

Etoposide 4'-hydrazide

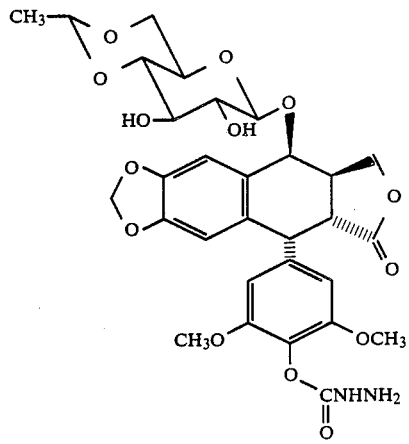

The 4'-chloroformate of etoposide was generated in situ from 2.00 g of etoposide as described in Example 22, and quenched with anhydrous hydrazine (0.86 ml, 27.2 mmol). The reaction mixture was stirred for 1.5 hr at 0° C., and then partitioned with ethyl acetate (250 ml) and phosphate buffer (pH 7.0, 100 ml). The organic layer was washed with brine and dried over K$_2$CO$_3$. Rotary evaporation followed by flash chromatography on silica gel using 4% methanol in ethyl acetate provided 1.52 g of the pure title compound as a colorless solid.

IR (KBr) 1774, 1604, 1507, 1488, 1424, 1390, 1339, 1238, 1163, 1132, 1100, 1078, 1038, 1004, 932 cm$^{-1}$.

300 MHz $^1$H NMR (CDCl$_3$/drop d6-DMSO) δ6.72 (s, 1H), 6.37 (s, 1H), 6.11 (s, 2H), 5.83 (d, 2H), 4.81 (d, 1H, J=3.0 Hz), 4.60 (q, 1H, J=4.9 Hz), 4.44 (d, 1H, J=4.9 Hz), 3.39–3.30 (m, 2H), 4.12–4.00 (m, 2H), 3.59–3.12 (m, 6H), 3.52 (s, 6H), 2.76–2.66 (m, 1H), 1.23 (d, 3H, J=4.9 Hz).

Mass spectrum (FAB), m/e, 647 (M$^+$+H). C$_{30}$H$_{34}$N$_2$O$_{14}$ requires M$^+$=646.

EXAMPLE 26

(a) Etoposide 4'-(2-dimethylaminoethyl) carbonate

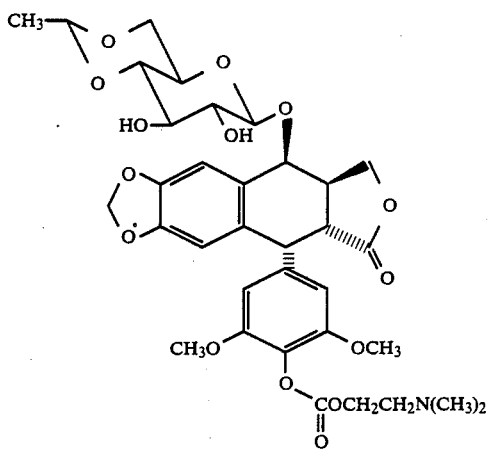

A magnetically stirred solution of etoposide (2.00 g, 3.40 mmol) in dry acetonitrile (250 ml) was treated with N,N-diisopropylethylamine (1.30 ml, 7.48 mmol) and cooled under N₂ to 0° C. To this solution was added phosgene (1.93M in toluene; 1.94 ml, 3.74 mmol) rapidly via syringe and the mixture was stirred for 5 min. at 0° C. 2-Dimethylaminoethanol (0.51 ml, 5.10 mmol) was added and the reaction mixture was stirred for 1 hr, after which time the solvent was removed in vacuo and the solid residue was dissolved in methylene chloride (300 ml). The solution was partitioned with saturated aqueous sodium bicarbonate (150 ml) and brine (150 ml) and dried over MgSO₄. Rotary evaporation followed by flash chromatography on silica gel using 5% methanol in methylene chloride provided 1.88 g (79%) of the pure title compound as a colorless solid.

IR (KBr) 1775, 1606, 1511, 1490, 1470, 1424, 1340, 1238, 1167,1136, 1100, 1080, 1040, 1005, 936 cm$^{-1}$.

300 MHz $^1$H NMR (CDCl₃) δ6.81 (s, 1H), 6.52 (s, 1H), 6.25 (s, 2H), 5.97 (d, 2H), 4.88 (d, 1H, J=3.4 Hz), 4.73 (q, 1H, J=5.0 Hz), 4.65–4.60 (m, 2H), 4.41 (m, 1H), 4.29 (t, 2H, J=6.0 Hz), 4.22 (dd, 1H), 4.15 (dd, 1H, J=6.1 and 10.6 Hz), 3.74 (m, 1H), 3.67 (s, 6H), 3.56 (m, 1H), 3.42 (m, 1H), 3.34–3.23 (m, 3H), 2.91–2.79 (m, 1H), 2.64 (t, 2H, J=6.0 Hz), 2.28 (s, 6H), 1.38 (d, 3H, J=5.0 Hz).

Mass spectrum (FAB), m/e, 704 (M⁺+H). C₃₄H₄₁NO₁₅ requires M⁺=703.

(b) Etoposide 4'-(2-dimethylaminoethyl) carbonate hydrochloride salt

A solution of the compound obtained in (a) above (510 mg, 0.725 mmol) in dry methylene chloride (50 ml) was cooled under N₂ to 0° C. and a solution of anhydrous hydrochloric acid (1.0M in ethyl ether; 870 μl, 0.87 mmol) was added thereto with stirring. The solvent was decanted from the resulting oily product and the residue was then triturated with ethyl ether (25 ml) to produce a crystalline material. The decanted solvent was diluted with ethyl ether (100 ml) to produce additional product. After filtration and drying in vacuo 50 mg (95%) of the pure title compound was obtained.

IR (KBr) 1775, 1606, 1512, 1487, 1467, 1422, 1340, 1238, 1161, 1132, 1098, 1079, 1038, 1004, 935 cm$^{-1}$.

300 MHz $^1$H NMR (CDCl₃) δ6.70 (s, 1H), 6.33 (s, 1H), 6.11 (s, 2H), 5.81 (dd, 2H), 4.80 (d, 1H, J=3.2 Hz), 4.58–4.51 (m, 3H), 4.42 (d, 1H, J=5.4 Hz), 4.34 (d, 1H, J=7.5 Hz), 4.31 (m, 1H), 4.08 (m, 1H), 4.00 (dd, 1H, J=4.3 and 10.1 Hz), 3.52 (s, 6H), 3.53–3.97 (m, 8H), 2.91–2.79 (m, 1H), 2.50 (br s, 6H), 1.20 (d, 3H, J=4.9 Hz).

Mass spectrum (FAB), m/e 704. C₃₄H₄₁NO₁₅. HCl requires M⁺+H=704.

EXAMPLE 27

(a) Etoposide 4'-2-dimethylaminoethyl)carbamate

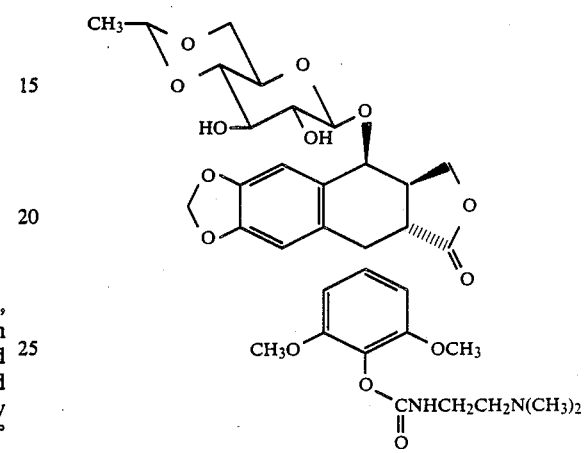

The procedure described in Example 26(a) was repeated using 2-dimethylaminoethylamine (0.56 ml, 5.10 mmol) instead of 2-dimethylaminoethanol to provide, after removal of acetonitrile, a crude solid. The solid was dissolved in methylene chloride and flash chromatographed on silica gel using 1 to 10% methanol in methylene chloride to provide 1.71 g (71.5%) of the pure title compound as a colorless solid.

IR (KBr) 1776, 1736, 1603, 1507, 1486, 1465, 1422, 1383, 1338, 1236, 1165, 1134, 1102, 1080, 1042, 1006 cm$^{-1}$.

300 MHz $^1$H NMR (CDCl₃) δ 6.81 (s, 1H), 6.54 (s, 1H), 6.24 (s, 2H), 5.97 (d, 2H), 5.79 (br t, 1H, NH), 4.88 (d, 1H, J=3.4 Hz), 4.73 (q, 1H, J=4.9 Hz), 4.58–4.50 (m, 2H), 4.41 (m, 1H), 4.24–4.13 (m, 2H), 3.71 (m, 1H), 3.67 (s, 6H), 3.57 (m, 1H), 3.44–3.20 (m, 6H), 2.91–2.79 (m, 1H), 2.52 (br t, 2H), 2.28 (s, 6H), 1.37 (d, 3H, J=4.9 Hz).

Mass spectrum (FAB), m/e, 703 (M⁺+H). C₃₄H₄₂N₂O₁₄ requires M⁺=702.

(b) Etoposide 4'-(2-dimethylaminoethyl)carbamate hydrochloride salt

A solution of the compound obtained in (a) above (503.7 mg, 0.717 mmol) in dry methylene chloride (125 m ) was cooled under N₂ to 0° C. To this solution was added, dropwise with magnetic stirring, a solution of anhydrous hydrochloric acid (1.0M in ethyl ether; 0.72 ml, 0.72 mmol). The reaction mixture was stirred at room temperature for 30 min., treated with ethyl ether (350 ml), and the resulting precipitate was collected by filtration and dried in vacuo to produce 395 mg (75%) of the pure title compound as a colorless solid.

IR (KBr) 1776, 1739, 1604, 1510, 1485, 1466, 1422, 1390, 1338, 1237, 1164, 1133, 1099, 1080, 1039, 1005 cm$^{-1}$.

300 MHz $^1$H NMR (CDCl₃/drop d6-DMSO) δ 7.32 (br t, 1H), 6.44 (s, 1H), 6.02 (s, 1H), 5.78 (s, 2H), 5.51 (s, 2H), 4.56 (d, 1H, J=4.2 Hz), 4.50 (d, 1H, J=3.3 Hz), 3.46 (d, 1H, J=3.9 Hz), 4.26 (q, 1H, J=4.9 Hz), 4.10 (d, 1H, J=5.3 Hz), 4.04 (d, 1H, J=7.6 Hz), 3.98 (m, 1H), 3.76 (m, 1H), 3.70 (dd, 1H), 3.18 (s, 6H), 3.20–2.70 (m, 8H), 2.39 (s, 6H), 0.88 (d, 3H, J=4.9 Hz).

Mass spectrum (FAB), m/e, 703. $C_{34}H_{42}N_2O_{14} \cdot HCl$ requires $M^+ + H = 703$.

EXAMPLE 28

(a) Etoposide 4'-(2-dimethylaminoethyl)thiocarbonate

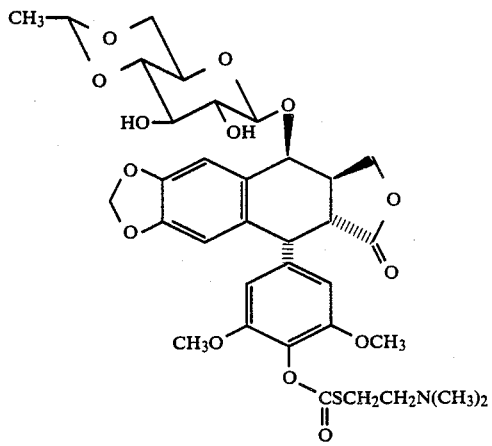

The procedure described in Example 26(a) was repeated using 2-dimethylaminoethanethiol hydrochloride (719 mg, 5.10 mmol) instead of 2-dimethylaminoethanol. The reaction was found to be complete in 3 hr. The solvent was removed in vacuo and the residue was dissolved in methylene chloride and flash chromatographed on silica gel using 5% methanol in methylene chloride to provide 821 mg (33.6%) of the pure title compound as a colorless solid.

IR (KBr) 1775, 1732, 1604, 1510, 1490, 1465, 1424, 1340, 1237, 1162, 1133, 1098, 1078, 1040, 1005, 933, 863, 765 cm$^{-1}$.

300 MHz $^1$H NMR (CDCl$_3$) δ 6.81 (s, 1H), 6.51 (s, 1H), 6.25 (s, 2H), 5.97 (dd, 2H), 4.89 (d, 1H, J=3.4 Hz), 4.73 (q, 1H, J=5 Hz), 4.64–4.60 (m, 2H), 4.41 (m, 1H), 4.24–4.13 (m, 2H), 3.73 (m, 1H), 3.67 (s, 6H), 3.56 (m, 1H), 3.41 (m, 1H), 3.38–3.23 (m, 3H), 3.02 (t, 2H), 2.89–2.79 (m, 1H), 2.59 (t, 2H), 2.26 (s, 6H), 1.37 (d, 3H, J=5 Hz).

(b) Etoposide 4'-(2-dimethylaminoethyl)thiocarbamate hydrochloride salt

The procedure described in Example 26(b) was repeated using the compound obtained in (a) above (459 mg, 0.639 mmol). After the addition of hydrochloric acid, the volume of the reation mixture was reduced in vacuo to 20 ml and ethyl ether (150 ml) was then added. The resulting precipitate was collected by filtration and dried in vacuo to produce 373 mg (81%) of the pure title compound.

IR (KBr) 1775, 1733, 1604, 1510, 1487, 1465, 1422, 1340, 1237, 1160, 1133, 1103, 1078, 1038, 1005 cm$^{-1}$.

300 MHz $^1$H NMR (CDCl$_3$) δ 6.81 (s, 1H), 6.50 (s, 1H), 6.27 (s, 2H), 5.99 (dd, 2H), 4.90 (d, 1H, J=3.4 Hz), 4.73 (q, 1H, J=5 Hz), 4.63–4.59 (m, 2H), 4.43 (m, 1H), 4.25–4.13 (m, 2H), 3.73 (m, 1H), 3.68 (s, 6H), 3.56 (m, 1H), 3.45–3.22 (m, 8H), 2.90–2.80 (m, 1H), 2.79 (s, 6H), 1.37 (d, 3H, J=5 Hz).

Mass spectrum (FAB), m/e 720 (M$^+$+H). $C_{34}H_{41}NO_{14}S$ requires $M^+ = 719$.

EXAMPLE 29

Etoposide 4'-methylsulfinylacetate

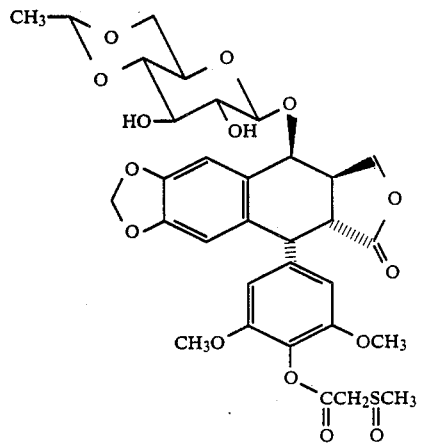

To a magnetically stirred solution of the compound of Example 6 (1.00 g, 1.48 mmol) in methylene chloride (50 ml) at −78° C. under N$_2$ was added meta-chloroperbenzoic acid (m-CPBA, 325 mg, 1.51 mmol, 80% from Aldrich) and the reaction mixture was allowed to stir for 1 h at −78° C. Additional m-CPEA (33 mg) was added and the reaction mixture was stirred at −78° C. for 1 h and then partitioned with saturated aqueous sodium bicarbonate (100 ml) and extracted with methylene chloride (5×50 ml). The combined organic extracts were washed with brine (100 ml) and dried over MgSO$_4$. Evaporation in vacuo provided 900 mg (86%) of the title compound, which was greater than 95% pure as determined by NMR and HPLC analysis.

IR (KBr) 1769, 1603, 1506, 1486, 1466, 1422, 1337, 1237, 1160, 1131, 1100, 1078, 1038, 1005, 961 cm$^{-1}$.

300 MHz $^1$H NMR (CDCl$_3$) δ 6.81 (s, 1H), 6.51 (s, 1H), 6.25 (br s, 2H), 5.95 (d, 2H), 4.87 (d, 1H), 4.72 (q, 1H), 4.61–4.58 (m, 2H), 4.40 (m, 1H), 4.26–4.08 (m, 3H), 3.82 (d, 1H, J=13.2 Hz), 3.70 (m, 1H), 3.64 (s, 6H), 3.55 (m, 1H), 3.40 (m, 1H), 3.33–3.25 (m, 3H), 2.90–2.80 (m, 1H), 2.83 (s, 3H), 1.36 (d, 3H, J-4.8 Hz).

Mass spectrum (FAB), m/e, 693.1869 (M$^+$+H). $C_{32}H_{36}O_{15}S$ requires 693.1853.

EXAMPLE 30

The general procedure described in Example 1 is repeated using the acid chlorides and 4'-demethylepipodophyllotoxin glucosides (formula I) listed below to provide the corresponding 4'-esters.

| Compound of formula (I) | acid chloride | product |
|---|---|---|
| R$^1$ = CH$_3$ | cyclohexanecarboxylic acid chloride | etoposide 4'-cyclohexanoate |
| " | cyclopropanecarboxylic acid chloride | etoposide 4'-cyclopropanoate |
| " | 5-fluoro-4-methyl benzoyl chloride | etoposide 4'-(5-fluoro-4-methyl)benzoate |
| " | phenylacetyl chloride | etoposide 4'-phenylacetate |
| " | 4-cyanobenzoyl chloride | etoposide 4'-(4-cyano)benzoate |
| " | methoxyacetyl chloride | etoposide 4'-methoxyacetate |

-continued

| Compound of formula (I) | acid chloride | product |
|---|---|---|
| " | 4-(4-methoxyphenyl)butyroyl chloride | etoposide 4'-(4-methoxyphenyl)butyrate |
| " | 4-nitrobenzoyl chloride | etoposide 4'-(4-nitro) benzoate |
| " | 2-mercaptobenzoyl chloride | etoposide 4'-(2-mercapto) benzoate |
| $R^1$ = $CH_3$ | 6-acetamidohexanoyl chloride | etoposide 4'-(6-acetamido) hexanoate |
| $R^1$ = $CH_3$ carboxyloate) | 2-quinoxalinecarbonyl chloride | etoposide 4'-(2-quinoxalinecarboxyloate) |
| $R^1$ = 2-thienyl | bromoacetyl chloride | teniposide 4'-bromoacetate |
| " | methylthioacetyl chloride | teniposide 4'-methylthioacetate |
| " | 4-dimethylamino- chloride | teniposide 4'-(4-dimethylamino) butyrate |
| " | isonicotinoyl chloride | teniposide 4'-isonicotinoate |
| $R^1$ = 2-thienyl | acryloyl chloride | teniposide 4' acrylate |
| " | octanoyl chloride | teniposide 4'-octanoate |
| " | benzoyl chloride | teniposide 4'-benzoate |

EXAMPLE 31

The general procedure described in Example 26 is repeated using the alcohols listed below to yield the corresponding 4'-carbonates.

| Alcohol | Product |
|---|---|
| allyl Alcohol | etoposide 4'-allyl carbonate |
| phenol | etoposide 4'-phenyl carbonate |
| 4-nitrophenol | etoposide 4'-(4-nitro)phenyl carbonate |
| 2-bromoethanol | etoposide 4'-(2-bromo)ethyl carbonate |
| isopropanol | etoposide 4'-isopropyl carbonate |

EXAMPLE 32

The general procedure of Example 21 is repeated using the amines listed below to provide the corresponding 4'-carbamates.

| amine | product |
|---|---|
| phenylamine | etoposide 4'-(N-phenyl) carbamate |
| piperidine | 4'-piperidylcarbonyl etoposide |
| allylamine | etoposide 4'-allylcarbamate |
| benzylamine | etoposide 4'-benzylcarbamate |
| 1,1-dimethylhydrazine | etoposide 4'-(1,1-dimethyl)hydrazide |
| ethylenediamine | etoposide 4'-(2-aminoethyl)carbamate |

What is claimed is:
1. A compound having the formula

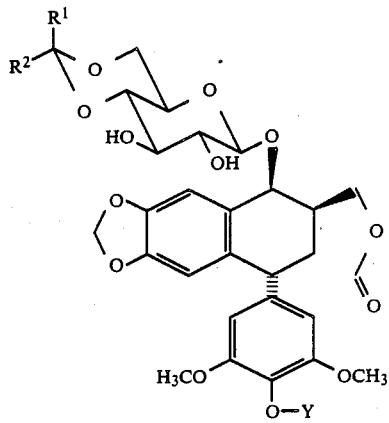

(XII)

wherein
$R^1$ and $R^2$ are each $C_{1-10}$alkyl; or $R^1$, $R^2$, and the carbon to which they are attached represent $C_{5-6}$cycloalkyl; or $R^1$ is H and $R^2$ is selected from the group consisting of $C_{1-10}$alkyl, $C_{2-10}$alkenyl, $C_{3-6}$cycloalkyl, furyl, thienyl, $C_{6-10}$aryl, and $C_{7-14}$aralkyl; and Y is $-C(O)-R^3$, $-C(O)-XR^4$, or $-C(O)-NR^5R^6$, wherein
X is oxygen or sulfur;
$R^3$ is selected from the group consisting of H, $C_{1-10}$alkyl, $C_{2-20}$alkenyl, $C_{3-6}$cycloalkyl, $C_{6-10}$aryl, $C_{7-14}$aralkyl, and heteroaryl selected from pyridyl, furyl, thienyl, pyrrolyl, pyrimidinyl, piperidinyl, and quinoxalinyl; each of the above groups is unsubstituted or substituted with one or more groups selected from hydroxy, $C_{1-6}$alkoxy, $C_{1-6}$alkanoyloxy, cyano, amino, quaternary ammonium, $C_{1-6}$alkylamino, di($C_{1-6}$)alkylamino, carboxy, $C_{1-6}$alkylthio, di($C_{1-6}$)alkylaminoalkyl($C_{2-6}$)thio, mercapto, mercaptothio, $C_{1-6}$alkanoylamino, nitro, $C_{1-6}$alkanoyl, carbamoyl, azido, $C_{1-6}$alkylsulfoxide, sulfone, and halogen; the substituents for the aryl, aralkyl, and heteroaryl groups additionally include $C_{1-6}$alkyl;

$R^4$ is selected from the group defined for $R^3$ with the exception that $R^4$ is not benzyl when X is oxygen, and $R^4$ is not H; or $R^4$ is anthraquinonyl-2-methylene; and $R^5$ and $R^6$ are each independently selected from the group defined for $R^3$; or $R^5$ is H and $R^6$ is selected from the group consisting of amine, $C_{1-6}$alkylamine, and di($C_{1-6}$)alkylamine; or $R^5$, $R^6$ and the N to which they are attached together form a 3- to 6-membered ring; or a pharmaceutically acceptable salt thereof.

2. A compound of claim 1 wherein $R^1$ is H, $R^2$ is selected from the group consisting of $C_{1-10}$ alkyl, phenyl and thienyl; and Y is $-C(O)R^3$, $-C(O)XR^4$, or $-C(O)NR^5R^6$ wherein X is oxygen or sulfur;

$R^3$ is selected from the group consisting of H; $C_{3-6}$cycloalkyl; $C_{2-20}$alkenyl; $C_{1-10}$alkyl; $C_{1-10}$alkyl substituted with one or more groups selected from the group consisting of halogen, azido, cyano, $C_{1-6}$alkylthio, di($C_{1-6}$)alkylamino, di($_{1-6}$)alkylamino($C_{2-6}$)alkylthio, quarternary ammonium, $C_{1-6}$alkylsulfoxide; phenyl; phenyl substituted with one or more groups selected from the group consisting of $C_{1-6}$alkyl, halogen, hydroxy, $C_{1-6}$alkoxy, mercapto, $C_{1-6}$alkylthio, cyano, and nitro; phenyl ($C_{1-6}$)alkyl wherein the phenyl ring is unsubstituted or substituted with one or more groups selected from the above list of phenyl substituents; and pyridyl;

$R^4$ is as defined above for $R^3$ with the exception that $R^4$ is not H and $R^4$ is not benzyl when X is oxygen; or $R^4$ is anthraquinonyl-2-methylene; and $R^5$ and $R^6$ are each independently selected from the group consisting of H; $C_{1-10}$alkyl; $C_{1-10}$alkyl substituted with one or more groups selected from the group consisting of halogen, hydroxy, $C_{1-6}$alkoxy, mercapto, $C_{1-6}$alkylthio, cyano, amino, $C_{1-6}$alkylamino, di($C_{1-6}$)alkylamino, and azido; or $R^5$ is H and $R^6$ is selected from the group consisting of $C_{3-6}$cycloalkyl, $C_{2-20}$alkenyl, phenyl, phenyl substituted with one or more groups selected from the list of phenyl substituents provided under $R^3$, phenyl ($C_{1-6}$)alkyl wherein the phenyl ring is unsubstituted or substituted with one or more groups selected from the list of phenyl substituents provided under $R^3$, amino, $C_{1-6}$alkylamino, di($C_{1-6}$)alkylamino, and pyridyl; or a pharmaceutically acceptable salt thereof.

3. A compound of claim 1 wherein $R^1$ is H and $R^2$ is methyl or 2-thienyl.

4. A compound of claim 1 wherein Y is —C(O)—$R^3$ and $R^3$ is selected from the group consisting of $C_{1-10}$alkyl; $C_{1-10}$alkyl substituted with one or more groups selected from halogen, azido, quaternary ammonium, $C_{1-6}$alkylthio, $C_{1-6}$alkylsulfoxide, di($C_{1-6}$)alkylamino, di($C_{1-6}$)alkylamino($C_{2-6}$)alkylthiol; $C_{2-20}$alkenyl; phenyl; and pyridyl; or a pharmaceutically acceptable salt thereof.

5. A compound of claim 4 wherein $R^1$ is H and $R^2$ is methyl.

6. A compound of claim 5 wherein $R^3$ is dimethylaminoethylthioethyl, or a pharmaceutically acceptable salt thereof.

7. The hydrochloride salt of a compound of claim 6.

8. A compound of claim 5 wherein $R^3$ is heptyl.

9. A compound of claim 5 wherein $R^3$ is bromomethyl.

10. A compound of claim 5 wherein $R^3$ is 3-bromopropyl.

11. A compound of claim 5 wherein $R^3$ is 3-iodopropyl.

12. A compound of claim 5 wherein $R^3$ is 3-azidopropyl.

13. A compound of claim 5 wherein $R^3$ is methylthiomethyl.

14. A compound of claim 5 wherein $R^3$ is methyl sulfinylmethyl.

15. A compound of claim 5 wherein $R^3$ is 3-(N,N-dimethylamino)propyl, or a pharmaceutically acceptable salt thereof.

16. The hydrochloride salt of a compound of claim 15.

17. A compound of claim 5 wherein $R^3$ is 3-ammonium acetate propyl.

18. A compound of claim 5 wherein $R^3$ is $C_{2-20}$alkenyl.

19. A compound of claim 18 wherein $R^3$ is ethylene.

20. A compound of claim 18 wherein $R^3$ is

—CH$_2$(CH$_2$)$_6$CH$\overset{Z}{=}$CHCH$_2$CH$\overset{Z}{=}$CH(CH$_2$)$_4$CH$_3$.

21. A compound of claim 5 wherein $R^3$ is phenyl.

22. A compound of claim 5 wherein $R^3$ is 4-pyridyl, or a pharmaceutically acceptable salt thereof.

23. The hydrochloride salt of a compound of claim 22.

24. A compound of claim 1 wherein Y is —C(O)—XR$^4$, wherein X is oxygen or sulfur and $R^4$ is selected from the group consisting of $C_{1-10}$alkyl; $C_{1-10}$alkyl sustituted with one or more groups selected from halogen and di($C_{1-6}$)alkylamino; p-nitrobenzyl; and anthraquinonyl-2-methylene; or a pharmaceutically acceptable salt thereof.

25. A compound of claim 24 wherein $R^1$ is H and $R^2$ is methyl.

26. A compound of claim 25 wherein X is oxygen.

27. A compound of claim 26 wherein $R^4$ is methyl.

28. A compound of claim 26 wherein $R^4$ is 2,2,2-trichloroethyl.

29. A compound of claim 26 wherein $R^4$ is p-nitrobenzyl.

30. A compound of claim 26 wherein $R^4$ is anthraquinonyl-2-methylene.

31. A compound of claim 24 wherein $R^4$ is 2-dimethylamino)ethyl, or a pharmaceutically acceptable salt thereof.

32. A compound of claim 25 wherein X is sulfur.

33. A compound of claim 32 wherein $R^4$ is 2-(dimethylamino)ethyl, or a pharmaceutically acceptable salt thereof.

34. A compound of claim 1 wherein Y is —C(O)—NR$^4$R$^6$, and $R^5$ and $R^6$ are independently selected from the group consisting of H, $C_{1-10}$alkyl; and $C_{1-10}$alkyl substituted with one or more groups selected from halogen and di($C_{1-6}$)alkylamino; or $R^5$ is H and $R^6$ is amino; or a pharmaceutically acceptable salt thereof.

35. A compound of claim 34 wherein $R^1$ is H and $R^2$ is methyl.

36. A compound of claim 35 wherein $R^5$ and $R^6$ are both 2-chloroethyl.

37. A compound of claim 35 wherein $R^5$ and $R^6$ are both H.

38. A compound of claim 35 wherein $R^5$ is H and $R^6$ is methyl.

39. A compound of claim 35 wherein $R^5$ and $R^6$ are both methyl.

40. A compound of claim 35 wherein $R^5$ is H and $R^6$ is 2-(dimethylamino)ethyl or a pharmaceutically acceptable salt thereof.

41. A compound of claim 35 wherein $R^5$ is H and $R^6$ is amine.

42. An intermediate having the formula

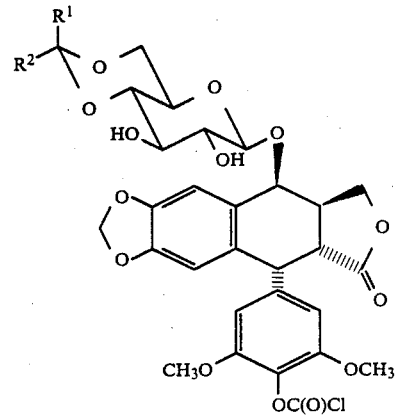

(XIII)

wherein $R^1$ and $R^2$ are as defined in claim 1.

43. An intermediate of claim 42 wherein $R^1$ is H and $R^2$ is methyl.

* * * * *